(12) United States Patent
Tsao et al.

(10) Patent No.: US 11,646,100 B2
(45) Date of Patent: May 9, 2023

(54) TARGET-ASSOCIATED MOLECULES FOR CHARACTERIZATION ASSOCIATED WITH BIOLOGICAL TARGETS

(71) Applicant: BillionToOne, Inc., Palo Alto, CA (US)

(72) Inventors: David Tsao, Palo Alto, CA (US); Oguzhan Atay, Palo Alto, CA (US)

(73) Assignee: BILLIONTOONE, INC., Palo Alto, CA (US)

( * ) Notice: Subject to any disclaimer, the term of this patent is extended or adjusted under 35 U.S.C. 154(b) by 1307 days.

(21) Appl. No.: 16/055,889

(22) Filed: Aug. 6, 2018

(65) Prior Publication Data
US 2019/0114389 A1 Apr. 18, 2019

Related U.S. Application Data

(60) Provisional application No. 62/541,555, filed on Aug. 4, 2017.

(51) Int. Cl.
*G16B 20/00* (2019.01)
*C12Q 1/6827* (2018.01)
(Continued)

(52) U.S. Cl.
CPC .............. *G16B 20/00* (2019.02); *C12N 15/10* (2013.01); *C12Q 1/68* (2013.01); *C12Q 1/6827* (2013.01);
(Continued)

(58) Field of Classification Search
CPC .......... G16B 20/00; G16B 5/00; G16B 25/00; G16B 30/00; G16B 50/00; C12N 15/10;
(Continued)

(56) References Cited

U.S. PATENT DOCUMENTS 8,195,415 B2   6/2012   Fan et al.
8,467,976 B2   6/2013   Lo et al.
(Continued)

FOREIGN PATENT DOCUMENTS

WO   WO 01/16367 A1   3/2001
WO   2011091046 A1   7/2011
(Continued)

OTHER PUBLICATIONS

Applied Biosystems, Application Note: Detection and Quantification of Sequence Variants from Sanger Sequencing 1 Traces, Determination of minor alleles by analyzing peak height dat, Retrieved from the internet:< URL: http://www.nstillcase.com/Downloads/seq-quantification-app-note.pdf>.
(Continued)

*Primary Examiner* — David A Vanore
(74) *Attorney, Agent, or Firm* — Fenwick & West LLP

(57) ABSTRACT

Embodiments of a method and/or system for facilitating characterization of one or more conditions can include: generating a set of target-associated molecules; generating a reference-associated set of molecule; facilitating generation of at least one spike-in mixture; determining one or more abundance metrics based on an analysis of the at least one spike-in mixture; and facilitating the characterization of the one or more conditions based on the one or more abundance metrics.

22 Claims, 16 Drawing Sheets

Specification includes a Sequence Listing.

(51) Int. Cl.
*C12Q 1/68* (2018.01)
*C12N 15/10* (2006.01)
*G16B 25/00* (2019.01)
*G16B 5/00* (2019.01)
*G16B 30/00* (2019.01)
*G16B 50/00* (2019.01)
*G01N 33/68* (2006.01)

(52) U.S. Cl.
CPC ............ *G01N 33/689* (2013.01); *G16B 5/00* (2019.02); *G16B 25/00* (2019.02); *G16B 30/00* (2019.02); *G16B 50/00* (2019.02); *C12Q 2600/166* (2013.01)

(58) Field of Classification Search
CPC .. C12Q 1/68; C12Q 1/6827; C12Q 2600/166; G01N 33/689
See application file for complete search history.

(56) References Cited

U.S. PATENT DOCUMENTS

| | | | |
|---|---|---|---|
| 8,688,388 | B2 | 4/2014 | Dzakula et al. |
| 8,706,422 | B2 | 4/2014 | Lo et al. |
| 8,877,442 | B2 | 11/2014 | Quake et al. |
| 9,512,480 | B2 | 12/2016 | Lo et al. |
| 9,944,973 | B2 | 4/2018 | Willey et al. |
| 10,287,630 | B2 * | 5/2019 | Xie ............... C12Q 1/6853 |
| 2002/0132278 | A1 | 9/2002 | Conover et al. |
| 2005/0106568 | A1 | 5/2005 | Kobayashi et al. |
| 2006/0088873 | A1 | 4/2006 | Su |
| 2007/0009884 | A1 | 1/2007 | Stoughton et al. |
| 2007/0092869 | A1 | 4/2007 | Fulmer-Smentek et al. |
| 2008/0124712 | A1 | 5/2008 | Hantash et al. |
| 2010/0105049 | A1 | 4/2010 | Ehrich et al. |
| 2010/0323352 | A1 | 12/2010 | Lo et al. |
| 2011/0033861 | A1 | 2/2011 | Wu et al. |
| 2011/0201507 | A1 | 8/2011 | Rava et al. |
| 2012/0021919 | A1 | 1/2012 | Scholl et al. |
| 2012/0270739 | A1 | 10/2012 | Rava et al. |
| 2013/0022973 | A1 | 1/2013 | Hansen et al. |
| 2013/0130923 | A1 | 5/2013 | Ehrich et al. |
| 2014/0195164 | A1 | 7/2014 | Lo et al. |
| 2015/0099266 | A1 | 4/2015 | Samuels et al. |
| 2015/0133391 | A1 | 5/2015 | De Vlaminick et al. |
| 2015/0152474 | A1 | 6/2015 | Pawlowski et al. |
| 2015/0284783 | A1 | 10/2015 | Canton |
| 2016/0040229 | A1 | 2/2016 | Talasaz et al. |
| 2016/0130649 | A1 | 5/2016 | Xie et al. |
| 2016/0138013 | A1 * | 5/2016 | Gole ............ C12N 15/1093 506/40 |
| 2016/0186262 | A1 * | 6/2016 | Johnson ............ C12Q 1/6869 506/2 |
| 2016/0222391 | A1 | 8/2016 | Krieg et al. |
| 2016/0251719 | A1 | 9/2016 | Umbarger |
| 2016/0304954 | A1 * | 10/2016 | Lin .................. C12Q 1/6869 |
| 2016/0319345 | A1 | 11/2016 | Gnerre et al. |
| 2016/0326589 | A1 * | 11/2016 | Al-Sedairy .......... C12Q 1/6883 |
| 2017/0175187 | A1 | 6/2017 | Rabinowitz et al. |
| 2017/0275691 | A1 | 9/2017 | Karius et al. |
| 2017/0327869 | A1 | 11/2017 | Schutz et al. |
| 2018/0023125 | A1 | 1/2018 | Talasaz et al. |
| 2018/0129781 | A1 * | 5/2018 | Bormann Chung ... G16B 40/10 |
| 2019/0066842 | A1 | 2/2019 | Zhang et al. |
| 2019/0078134 | A1 | 3/2019 | Spaulding et al. |
| 2019/0114389 | A1 | 4/2019 | Tsao et al. |
| 2019/0147980 | A1 * | 5/2019 | Landry ............. C12Q 1/6883 435/6.12 |
| 2019/0211395 | A1 | 7/2019 | Tsao et al. |
| 2020/0080141 | A1 * | 3/2020 | Weng ............... C12Q 1/6874 |
| 2020/0087723 | A1 | 3/2020 | Halpern et al. |

FOREIGN PATENT DOCUMENTS

| | | | | |
|---|---|---|---|---|
| WO | 2011156795 | A2 | 12/2011 | |
| WO | WO 2012/012703 | A2 | 1/2012 | |
| WO | 2012058316 | A1 | 5/2012 | |
| WO | WO 2012/109500 | A2 | 8/2012 | |
| WO | 2012129363 | A2 | 9/2012 | |
| WO | WO-2013016712 | A2 * | 1/2013 | ........... C12N 15/111 |
| WO | WO-2013181170 | A1 * | 12/2013 | ........... C12Q 1/6844 |
| WO | WO 2014/023167 | A1 | 2/2014 | |
| WO | 2014039556 | A1 | 3/2014 | |
| WO | 2014082032 | A1 | 5/2014 | |
| WO | WO-2014116881 | A1 * | 7/2014 | ........... C12Q 1/6869 |
| WO | WO 2017/020024 | A2 | 2/2017 | |
| WO | 2017165864 | A1 | 9/2017 | |
| WO | 2017210372 | A1 | 12/2017 | |
| WO | 2018031486 | A1 | 2/2018 | |
| WO | 2014127484 | A1 | 11/2018 | |
| WO | WO 2019/028470 | A2 | 2/2019 | |
| WO | WO-2019028462 | A1 * | 2/2019 | ............. C12N 15/10 |
| WO | WO 2019/135790 | A1 | 7/2019 | |

OTHER PUBLICATIONS

Darr, I. M., et al., "Inferring relative proportions of DNA variants from sequencing electropherograms", Bioinformatics, vol. 25, Issue 24, hllps://doi.org/10.1093/bioinformatics/btp583, Oct. 9, 2009, 3244-3250.

Curci, Pasquale Luca, et al., "How a Small Double-Stranded Trick Can Mislead Sanger Sequencing", J Biomol Tech. vol. 26, Issue 3, Sep. 1, 2015, 80-82.

International Search Report and the Written Opinion of the International Searching Authority, Application No. PCT/US18/45419, dated Dec. 21, 2018.

Kaboev, 0. K., et al., "PCR hot start using primers with the structure of molecular beacons {hairpin-like structure)", Nucl Acids Res, Sep. 12, 2000, vol. 28, No. 21.

Tourlousse, Dieter M., et al., "Synthetic spike-in standards for high-throughput 16S rRNA gene amplicon 4 sequencing", Biomedical Research Institute, National Institute of Advanced Industrial Science and Technology, Dec. 15, 2016.

International Search Report and Written Opinion for PCT Application No. PCT/US2018/045434 dated Nov. 29, 2018.

International Preliminary Report on Patentability for PCT/US2018/045394, dated Feb. 4, 2020.

International Preliminary Report on Patentability for PCT/US2018/045419, dated Feb. 4, 2020.

United States Office Action, U.S. Appl. No. 16/252,344, filed Nov. 2, 2021, eight pages.

European Patent Office, European Search Report and Opinion, EP Patent Application No. 19846965.2, dated Jun. 1, 2021, seven pages.

European Patent Office, European Search Report and Opinion, EP Patent Application No. 18841140.9, dated Apr. 21, 2021, 11 pages.

Rowe, D.T. et al., "Use of Quantitative Competitive PCR to Measure Epstein-Barr Virus Genome Load in the Peripheral Blood of Pediatric Transplat Patients with Lymphoproliferative Disorders," Journal of Clinical Microbiology, vol. 35, No. 6, Jun. 1997, pp. 1612-1615.

Yuan, J. et al., "A competitive PCR assay confirms the association of a copy number variation in the VIPR2 gene with schizophrenia in Han Chinese," Schizophrenia Research, vol. 156, Apr. 29, 2014, pp. 66-70.

Zentilin, L. et al., "Competitive PCR for precise nucleic acid quantification," Nature Protocols, vol. 2, No. 9, Aug. 23, 2007, pp. 2092-2104.

"International Search Report and the Written Opinion, Application No. PCT/US19/014340, dated Mar. 29, 2019."

Yan, Ti-Zhen, et al., "Reliable Detection of Paternal SNPs within Deletion Breakpoints for Non-Invasive Prenatal Exclusion of Homozygous a-Thalassemia in Maternal Plasma", PLoS One, Sep. 29, 2011, vol. 6, No. 9, e24779, pp. 1-9.

(56) References Cited

OTHER PUBLICATIONS

International Search Report and Written Opinion for PCT Application No. PCT/US2018/045394 dated Oct. 10, 2018.
Lun, Fiona M.F., et al., "Noninvasive prenatal diagnosis of monogenic diseases by digital size selection and relative mutation dosage on DNA in maternal plasma.", PNAS vol. 105, Dec. 16, 2008, 19920-19925.
Quail, M. A., et al., "SASI-Seq: sample assurance Spike-Ins, and highly differentiating 384 barcoding for Illumina sequencing.", BMC Genomics, 2014, 1-12.
Silas, S., et al., "Direct CRISPR spacer acquisition from RNA by a natural reverse transcriptase-Cas1 fusion protein.", Science, Feb. 26, 2016, 1-31.
Sinha, R., et al., "Index Switching Causes "Spreading-Of-Signal" Among Multiplexed Samples In Illumina HiSeq 4000 DNA Sequencing ", Apr. 9, 2017, 1-29.
International Preliminary Report on Patentability for PCT/US18/45434, dated Jul. 14, 2020.
International Search Report and the Written Opinion, Application No. PCT/US19/45331, dated Oct. 25, 2019.
Tsao, et al. "A novel high-throughput molecular counting method with single base-pair resolution enables accurate single-gene NIPT," bioRxiv, Apr. 3, 2019 (Apr. 3, 2019), pp. 1-20.

\* cited by examiner

FIGURE 7A

SEQUENCE LISTING

```
<160> NUMBER OF SEQ ID NOS: 19

<210> SEQ ID NO 1
<211> LENGTH: 119
<212> TYPE: DNA
<213> ORGANISM: Homo sapiens

<400> SEQUENCE: 1
gggtccagaa atacgtcagt gacctggagc tgagtgcctg aggggtccag aagcttcgag      60
gcccagcgac ctcagtgggc ccagtgggga ggagcaggag cctgagcctt gggaacatg     119

<210> SEQ ID NO 2
<211> LENGTH: 119
<212> TYPE: DNA
<213> ORGANISM: Artificial Sequence
<220> FEATURE:
<223> OTHER INFORMATION: Synthetic construct

<400> SEQUENCE: 2
gggtccagaa atacgtcagt gacctggagc gcctgagggg tccagaagct tcgaggccca      60
gcgacctcag tgggcccagt gggtgagtga ggagcaggag cctgagcctt gggaacatg     119

<210> SEQ ID NO 3
<211> LENGTH: 118
<212> TYPE: DNA
<213> ORGANISM: Homo sapiens

<400> SEQUENCE: 3
gcagtaacgg cagacttctc ctcaggagtc agatgcacca tggtgtctgt ttgaggttgc      60
tagtgaacac agttgtgtca gaagcaaatg taagcaatag atggctctgc cctgactt     118

<210> SEQ ID NO 4
<211> LENGTH: 118
<212> TYPE: DNA
<213> ORGANISM: Artificial Sequence
```

```
<220> FEATURE:
<223> OTHER INFORMATION: Synthetic construct

<400> SEQUENCE: 4
gcagtaacgg cagacttctc ctcaggagtg caccatggtg tctgtttgag gttgctagtg      60
aacacagttg tgtcagaagc aaatgttcag aaagcaatag atggctctgc cctgactt      118

<210> SEQ ID NO 5
<211> LENGTH: 118
<212> TYPE: DNA
<213> ORGANISM: Artificial Sequence
<220> FEATURE:
<223> OTHER INFORMATION: Synthetic construct

<400> SEQUENCE: 5
gcagtaacgg cagacttctc cacaggagaa tgttcagatg caccatggtg tctgtttgag      60
gttgctagtg aacacagttg tgtcagaagc aaagcaatag atggctctgc cctgactt      118

<210> SEQ ID NO 6
<211> LENGTH: 143
<212> TYPE: DNA
<213> ORGANISM: Homo sapiens

<400> SEQUENCE: 6
ggcatctggc catattgcat ctactttcat gatattcgga aatgctaatg attacctttt      60
tctgatagat acatgcacag aaacagagaa ataacaagaa ttaagaggga agagatcaag     120
agactgaaag attacctcac ggt                                             143

<210> SEQ ID NO 7
<211> LENGTH: 143
<212> TYPE: DNA
<213> ORGANISM: Artificial Sequence
<220> FEATURE:
<223> OTHER INFORMATION: Synthetic construct

<400> SEQUENCE: 7
ggcatctggc catattgcat ctactttcat gtatactaag gatgctaatg attacctttt      60
tctgatagat acatgcacag aaacagagaa ataacaagaa ttaagaggga agagatcaag     120
agactgaaag attacctcac ggt                                             143

<210> SEQ ID NO 8
<211> LENGTH: 120
<212> TYPE: DNA
<213> ORGANISM: Homo sapiens

<400> SEQUENCE: 8
gcaccacatt ccgtaaagat gatttcccaa gtaacggtat ttgactaagt tgctccagag      60
tgttagggtg caaaccacag ttagtaagct ccttatgaac aacctcctgt ggaaatgtgt     120

<210> SEQ ID NO 9
<211> LENGTH: 120
<212> TYPE: DNA
<213> ORGANISM: Artificial Sequence
<220> FEATURE:
<223> OTHER INFORMATION: Synthetic construct

<400> SEQUENCE: 9
gcaccacatt ccgtaaagat gatttcccaa gttctatata gggactaagt tgctccagag      60
tgttagggtg caaaccacag ttagtaagct ccttatgaac aacctcctgt ggaaatgtgt     120
```

<210> SEQ ID NO 10
<211> LENGTH: 121
<212> TYPE: DNA
<213> ORGANISM: Homo sapiens

<400> SEQUENCE: 10

```
taccggtaat tccttggcta gctttattac catattttca agatattctg gtaaacttttt    60
aaactgctgg ttggttggct ggaagaagtg agggcttctc cgtgctaata gtctcagggc   120
t                                                                   121
```

<210> SEQ ID NO 11
<211> LENGTH: 121
<212> TYPE: DNA
<213> ORGANISM: Artificial Sequence
<220> FEATURE:
<223> OTHER INFORMATION: Synthetic construct

<400> SEQUENCE: 11

```
taccggtaat tccttggcta gctttattac catagaactt tttaattctg gtaaacttttt    60
aaactgctgg ttggttggct ggaagaagtg agggcttctc cgtgctaata gtctcagggc   120
t                                                                   121
```

<210> SEQ ID NO 12
<211> LENGTH: 123
<212> TYPE: DNA
<213> ORGANISM: Homo sapiens

<400> SEQUENCE: 12

```
ggagttttaa cattgaatgc ggagaacact aattatgcct atcaagttcc aaacttccat    60
aaatgtgaaa tctgtctact atcttttcca aaagaatccc agtttcaacg ccacatgagg   120
gat                                                                 123
```

<210> SEQ ID NO 13
<211> LENGTH: 123
<212> TYPE: DNA
<213> ORGANISM: Artificial Sequence
<220> FEATURE:
<223> OTHER INFORMATION: Synthetic construct

<400> SEQUENCE: 13

```
ggagttttaa cattgaatgc ggagaacact aattagtatc caactgttcc aaacttccat    60
aaatgtgaaa tctgtctact atcttttcca aaagaatccc agtttcaacg ccacatgagg   120
gat                                                                 123
```

<210> SEQ ID NO 14
<211> LENGTH: 129
<212> TYPE: DNA
<213> ORGANISM: Homo sapiens

<400> SEQUENCE: 14

```
accaggtatc catcatccca cgtggcaaag gactaggtta tgctcagtat ttaccaaaag    60
aacaatacct ctataccaaa gagcagctct tggataggat gtgtatgact ttaggtggtc   120
gagtctctg                                                           129
```

<210> SEQ ID NO 15
<211> LENGTH: 129
<212> TYPE: DNA
<213> ORGANISM: Artificial Sequence

```
<220> FEATURE:
<223> OTHER INFORMATION: Synthetic construct

<400> SEQUENCE: 15
accaggtatc catcatccca cgtggcaaag gactaggtta tgctcagtat ttaccaaaag    60
aacaatacct ctataccaaa gagcagcctg gtttagagat gtgtatgact ttaggtggtc   120
gagtctctg                                                           129

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
gggtccagaa atacgtcagt                                                20

<210> SEQ ID NO 17
<211> LENGTH: 18
<212> TYPE: DNA
<213> ORGANISM: Artificial Sequence
<220> FEATURE:
<223> OTHER INFORMATION: Synthetic construct

<400> SEQUENCE: 17
catgttccca aggctcag                                                  18

<210> SEQ ID NO 18
<211> LENGTH: 22
<212> TYPE: DNA
<213> ORGANISM: Artificial Sequence
<220> FEATURE:
<223> OTHER INFORMATION: Synthetic construct

<400> SEQUENCE: 18
gcagtaacgg cagacttctc ca                                             22

<210> SEQ ID NO 19
<211> LENGTH: 21
<212> TYPE: DNA
<213> ORGANISM: Artificial Sequence
<220> FEATURE:
<223> OTHER INFORMATION: Synthetic construct

<400> SEQUENCE: 19
aagtcagggc agagccatct a                                              21
```

TARGET-ASSOCIATED MOLECULES FOR CHARACTERIZATION ASSOCIATED WITH BIOLOGICAL TARGETS

CROSS-REFERENCE TO RELATED APPLICATIONS

This application claims the benefit of U.S. Provisional Application Ser. No. 62/541,555, filed on 4 Aug. 2017, which is incorporated herein in its entirety by this reference.

TECHNICAL FIELD

This disclosure relates generally to the field of genomics.

REFERENCE TO SEQUENCE LISTING SUBMITTED VIA EFS-WEB AS ASCII TEXT FILE

The Sequence Listing in file "BLLN-P02-US-SEQ-LST-PatentIn_ST25.txt" created on 19 Dec. 2018, 5,422 bytes, machine format IBM-PC, MS-Windows operating system, in accordance with 37 C.F.R. §§ 1.821- to 1.825, is hereby incorporated by reference in its entirety for all purposes.

BRIEF DESCRIPTION OF THE FIGURES

FIGS. 7A-7B include specific examples of target-associated molecules (hg19=SEQ ID NO: 1; CCL31 spk=SEQ ID NO: 2) and applying the target-associated molecules for detecting copy number variants;

DESCRIPTION OF THE EMBODIMENTS

Figure 1A:
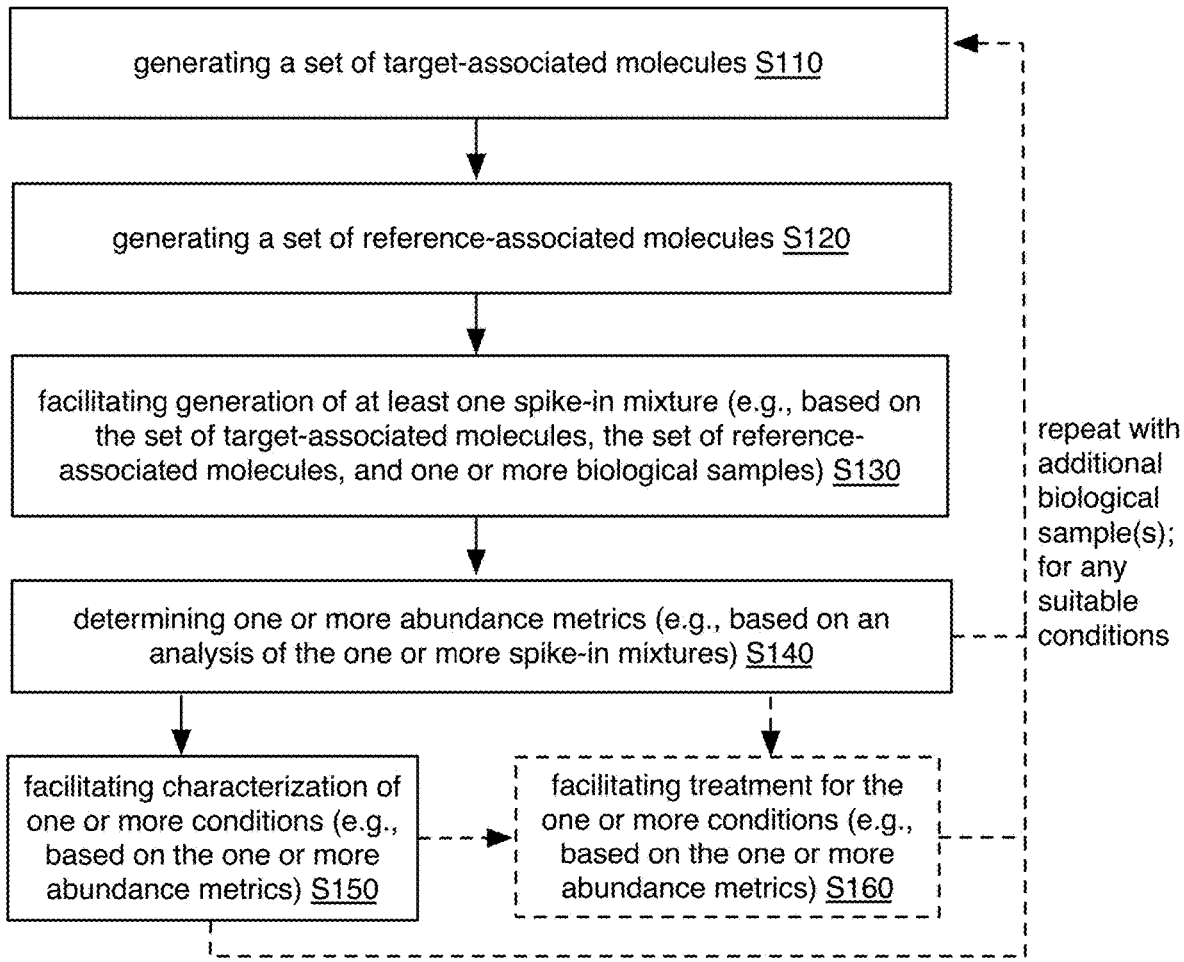
FIGS. 1A-1C include flowchart representations of variations of an embodiment of a method.
Figure 1B:
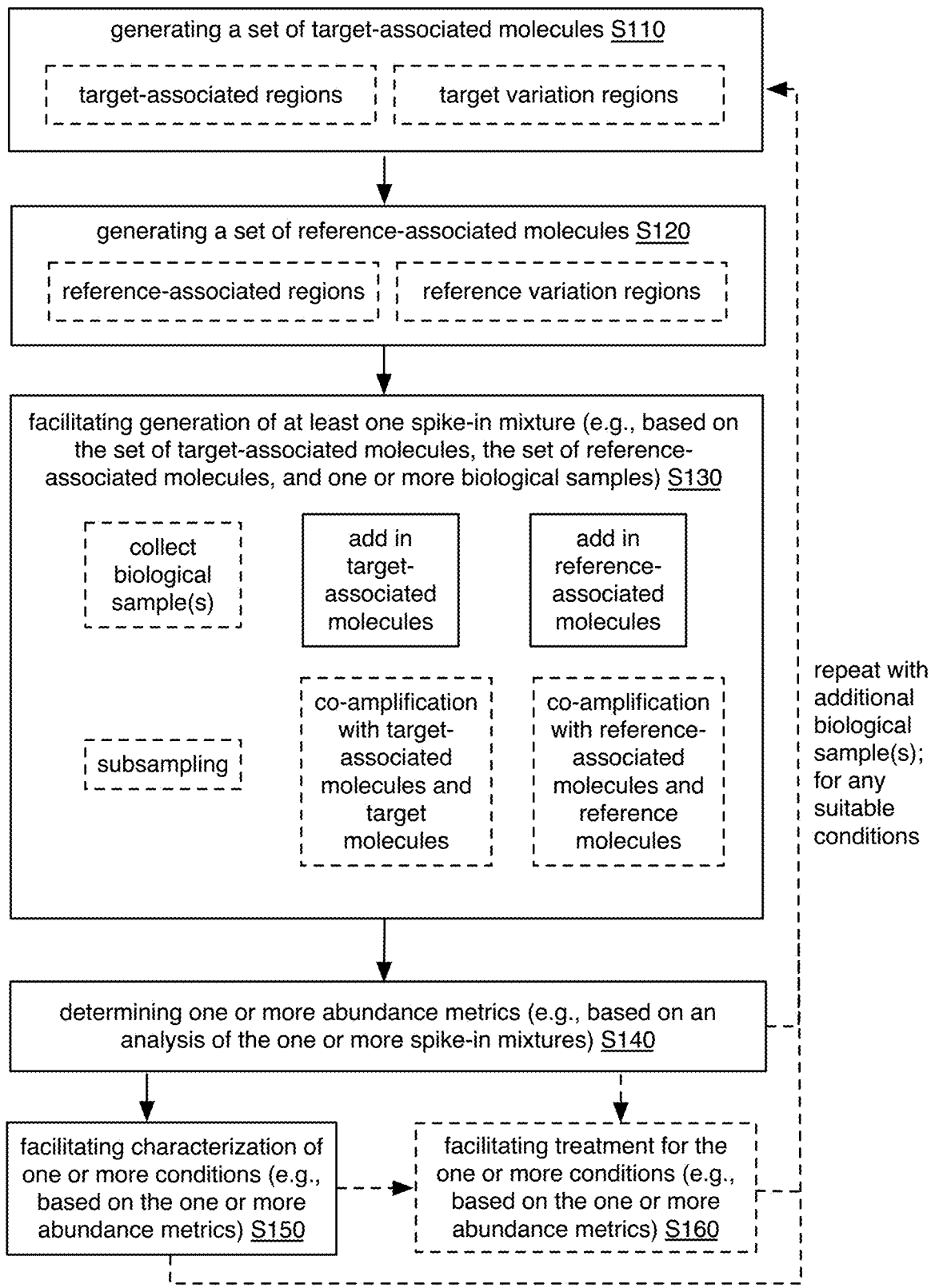
Figure 1C:
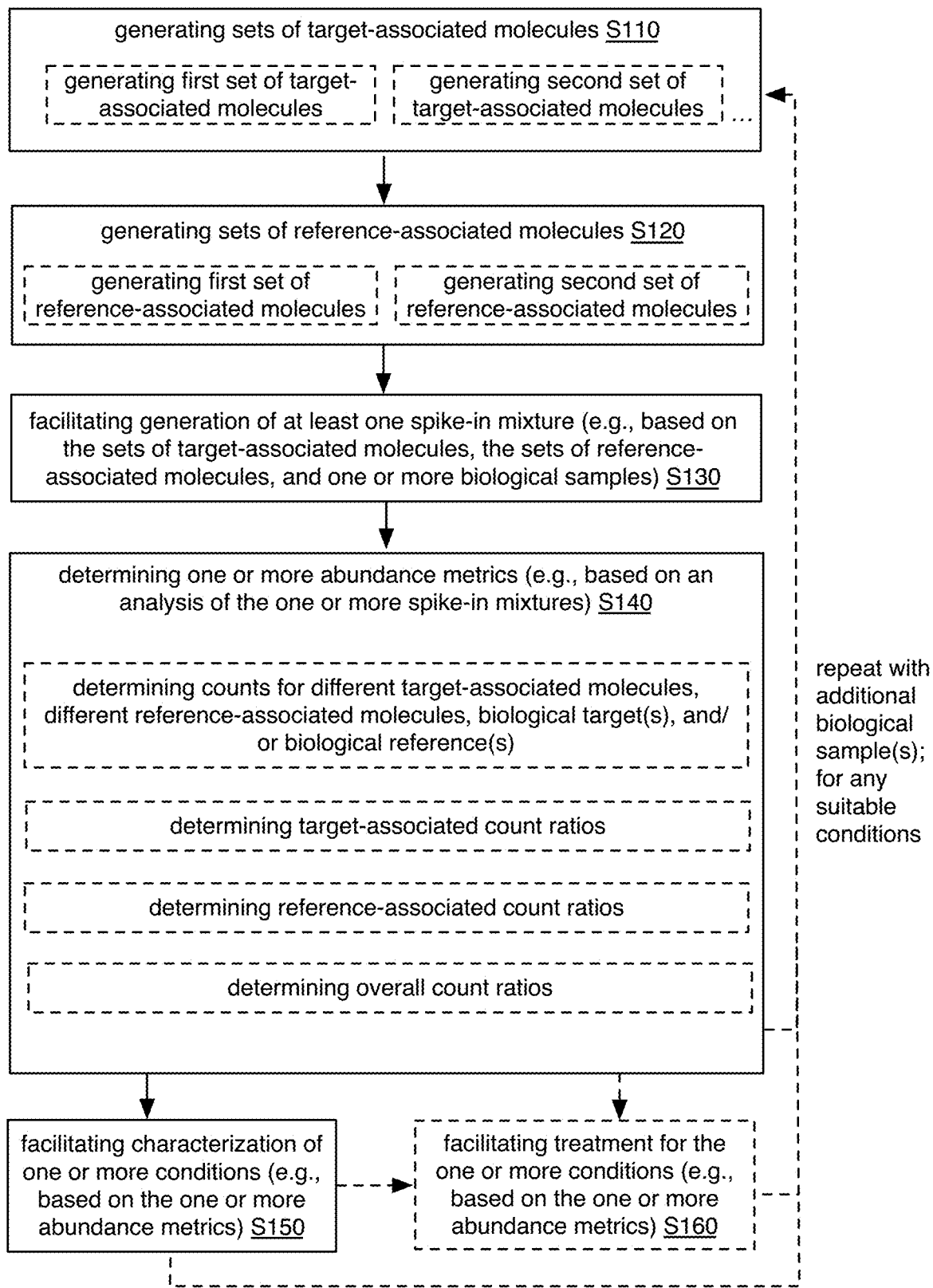

The following description of the embodiments (e.g., including variations of embodiments, examples of embodiments, specific examples of embodiments, other suitable variants, etc.) is not intended to be limited to these embodiments, but rather to enable any person skilled in the art to make and use.

1. Overview.

As shown in FIGS. 1A-1C, 2-3, and 5-6, embodiments of a method 100 (e.g., for facilitating characterization of one or more conditions, such as one or more medical conditions, such as one or more genetic disorders, etc.) can include: generating a set of target-associated molecules (e.g., associated with one or more target molecules associated with the one or more conditions; etc.) S110; generating a set of reference-associated molecules (e.g., associated with one or more reference molecules; etc.) S120; facilitating generation of at least one spike-in mixture (e.g., one or more spike-in mixtures; one or more mixtures generated based on spiking-in target-associated molecules and/or reference-associated molecules) S130, such as based on processing the set of target-associated molecules and the set of reference-associated molecules with a biological sample (e.g., a biological sample including target molecules and/or reference molecules; a biological sample from a user; etc.), such as where the spike-in mixtures can enable increased accuracy (e.g., through minimization of amplification biases, such as through generation of the spike-in mixtures from co-amplification; etc.) in abundance determination (e.g., for facilitating the characterization of the one or more conditions; etc.); determining one or more abundance metrics (e.g., a comparison between a target-associated abundance metric such as a target-associated count ratio, and a reference-associated abundance metric such as a reference-associated count ratio; a target-associated count metric relative to a reference-associated count metric), such as based on an analysis (e.g., sequencing operation, etc.) of the at least one spike-in mixture (e.g., based on sequence reads from sequencing the at least one spike-in mixtures; etc.) S140; and/or facilitating the characterization of the one or more conditions based on the one or more abundance metrics S150.

Additionally or alternatively, embodiments of the method 100 can include facilitating treatment S160 (e.g., of the one or more conditions based on the one or more abundance metrics, etc.) and/or any other suitable process.

In a specific example, the method 100 can include: generating a set of target-associated nucleic acids (e.g., a target-associated spike-in), where nucleic acids of the set of target-associated nucleic acids include target-associated sequences (e.g., a nucleotide sequence matching a target sequence region of a target molecule in the biological sample, such as a target molecule corresponding to a biological target associated with a medical condition; etc.) associated with a target chromosome (and/or other suitable biological target; etc.) (e.g., chromosome 21, where different sets of target-associated nucleic acids can be generated, such as where each set can correspond to a different loci of chromosome 21 and/or can include target-associated regions including nucleic acid sequences matching a target sequence region for the corresponding loci; etc.), and include variation regions (e.g., including a variation sequence with one or more mutations, polymorphisms, and/or modifications to a target sequence identifying chromosome 21, etc.); generating a set of reference nucleic acids (e.g., a reference spike-in), where nucleic acids of the set of reference-associated nucleic acids include reference-associated sequences associated with a reference chromosome (and/or other suitable biological reference) (e.g., chromosome 18, where different sets of reference-associated nucleic acids can be generated, such as where each set can correspond to a different loci of chromosome 18 and/or can include reference-associated regions including nucleic acid sequences matching a reference sequence region for the corresponding loci; etc.), and can include variation regions (e.g., including a variation sequence with one or more mutations, polymorphisms, and/or modifications to a reference sequence identifying chromosome 18, etc.); combining the set of target-associated nucleic acids and the set of reference-associated nucleic acids with a biological sample (e.g., using equal abundances of the set of target-associated nucleic acids and the set of reference-associated nucleic acids; where the biological sample includes a blood sample from a pregnant female; etc.); amplifying the set of target-associated nucleic acids and target nucleic acids (e.g., endogenous DNA molecules identifying chromosome 21) from the biological sample based on a set of target-associated primers (e.g., targeting a sequence shared by the target-associated nucleic acids and the target nucleic acids); amplifying the set of reference-associated nucleic acids and reference nucleic acids (e.g., endogenous DNA molecules identifying chromosome 18) from the biological sample based on a set of reference-associated primers (e.g., targeting a sequence shared by the reference-associated nucleic acids and the reference nucleic acids); determining a target-associated count ratio between a first count of target nucleic acids including the target sequence (e.g., a sequence read count for target molecules corresponding to the biological target; etc.) and a second count of target-associated nucleic acids (e.g., a sequence read count corresponding to the spike-in molecules), where individual count ratios associated with different target sequences (e.g., corresponding to different loci of chromosome 21) can be combined to determine an overall count ratio; determining a reference-associated count ratio between a first count of reference nucleic acids including the reference sequence (e.g., a sequence read count for reference molecules corresponding to the biological reference; etc.) and a second count of reference-associated nucleic acids (e.g., a count of the spike-in reference molecules), where individual reference-associated count ratios associated with different reference sequences (e.g., corresponding to different loci of chromosome 18) can be combined to determine an overall reference-associated count ratio; and/or characterizing (e.g., detecting; diagnosing; etc.) one or more medical conditions (e.g., Down syndrome; etc.) for a user (e.g., the user providing the biological sample; etc.) based on a comparison between the target-associated count ratio and the reference-associated count ratio (e.g., when the target-associated count ratio corresponding to chromosome 21 exceeds the reference-associated count ratio corresponding to chromosome 18 beyond a statistically significant threshold amount, etc.).

In a specific example, the method 100 (e.g., for facilitating prenatal diagnosis of a genetic disorder from a maternal sample associated with a pregnant woman, etc.) can include generating a set of target-associated molecules (e.g., target-associated nucleic acid molecules; etc.) including target-associated regions with sequence similarity to a target sequence region of an biological target (e.g., HbS mutated hemoglobin; etc.) associated with the genetic disorder (e.g., sickle cell disease; etc.); and target variation regions with sequence dissimilarity to a sequence region (e.g., a sequence region adjacent in sequence position to the target sequence region; a sequence region proximal in sequence position to the target sequence region; etc.) of the biological target; generating a set of reference-associated molecules including reference-associated regions with sequence similarity to a reference sequence region of an endogenous reference molecule (e.g., HbA normal hemoglobin; etc.); and reference variation regions with sequence dissimilarity to a sequence region of the endogenous reference molecule; generating a first spike-in mixture based on amplifying the set of target-associated molecules and first nucleic acid molecules from the maternal sample (e.g., using primers targeting sequences corresponding to the sequence similarity between the target-associated regions and the target sequence regions, such as for facilitating co-amplification; through polymerase chain reaction (PCR) with the primers; etc.), where the first nucleic acid molecules (e.g., nucleic acids; nucleic acid fragments; fetal nucleic acid molecules; nucleic acid molecules from the mother; etc.) include the target sequence region; generating a second spike-in mixture (e.g. via a separate sample processing container and set of sample processing operations from co-amplification of the set of target-associated molecules and the first nucleic acid molecules; via the same sample processing container and set of sample processing operations as the co-amplification of the set of target-associated molecules and the first nucleic acid molecules; where amplification operations can be performed in the same container for first, second, and/or any suitable co-amplification using the same amplification operations, in separate containers using separate containers; where any suitable number of containers can be used for any suitable number of mixtures; such as where the first and the second spike-in mixtures and/or any suitable mixtures are in the same or different containers; etc.) based on amplifying the set of reference-associated molecules and second nucleic acid molecules (e.g., nucleic acids; nucleic acid fragments; fetal nucleic acid molecules; nucleic acid molecules from the mother; etc.) from the maternal sample, where the second nucleic acid molecules include the reference sequence region; sequencing (e.g., via high-throughput sequencing, etc.) the first and the second spike-in mixtures (e.g., in a single container; in different containers; in a plurality of containers; etc.) to determine a read count for the endogenous biological target (e.g., sequence read count for sequences including the target sequence region; sequence read count for target molecules corresponding to the biological target; etc.), a read count for the set of target-associated molecules (e.g., sequence read count for sequences corresponding to the target-associated molecules; sequence read count for target-associated molecules; etc.), a read count for the endogenous reference molecule (e.g., sequence read count for sequences including the reference sequence region; etc.), and a read count for the set of reference-associated molecules (e.g., sequence read count for sequences corresponding to the reference-associated molecules; etc.); determining a target-associated count ratio based on the read count for the biological target and the read count for the set of target-associated molecules (e.g., target-associated count ratio of sequence read count for endogenous HbS to sequence read count for HbS spike-in molecules; etc.); determining a reference-associated count ratio based on the read count for the endogenous reference molecule and the read count for the set of reference-associated molecules (e.g., reference-associated count ratio of sequence read count for endogenous HbA to sequence read count for HbA spike-in molecules; etc.); and/or facilitating the prenatal diagnosis of the genetic disorder based on a comparison between the target-associated count ratio and the reference-associated count ratio.

In a specific example, the method 100 (e.g., for facilitating characterization of a medical condition from a biological sample, etc.) can include generating a set of target-associated molecules including target-associated regions with sequence similarity to a target sequence region of a biological target (e.g., where the set of target-associated molecules can additionally or alternatively include target variation regions with sequence dissimilarity to a sequence region of the biological target; etc.); generating a set of reference-associated molecules including reference-associated regions with sequence similarity to a reference sequence region of a biological reference (e.g., where the set of reference-associated molecules can additionally or alternatively include reference variation regions with sequence dissimilarity to a sequence region of the biological reference; etc.); facilitating generation of at least one spike-in mixture, where the generation of the at least one spike-in mixture (e.g., one or more spike-in mixtures; etc.) includes amplification of the set of target-associated molecules, the set of reference-associated molecules, first nucleic acid molecules from the biological sample, and second nucleic acid molecules from the biological sample (e.g., co-amplification of the set of target-associated molecules and the first nucleic acid molecules, such as with a first set of primers targeting the set of target-associated molecules and the first nucleic acid molecules, such as based on the sequence similarity; co-amplification of the first set of reference-associated molecules and the second nucleic acid molecules, such as in the same or different sample compartments using same, similar, or different sample processing operations, such as with a second set of primers targeting the set of reference-associated molecules and the second nucleic acid molecules, such as based on the sequence similarity; etc.), where the first nucleic acid molecules are associated with (e.g., include; etc.) the target sequence region (and/or the sequence regions to which the target variation regions include sequence dissimilarity; etc.), and where the second nucleic acid molecules are associated with (e.g., include; etc.) the reference sequence region (and/or the sequence regions to which the reference variation regions include sequence dissimilarity; etc.); determining at least one abundance metric associated with the biological target, the set of target-associated molecules, the biological reference, and the set of reference-associated molecules, based on sequence reads from sequencing of the at least one spike-in mixture (e.g., determining a count for the biological target, a count for the set of target-associated molecules, a count for the biological reference, and a count for the set of reference-associated molecules, based on sequencing of the at least one spike-in mixture; determining a target-associated count ratio and a reference-associated count ratio based on the count for the biological target, the count for the first set of target-associated molecules, the count for the biological reference, and the count for the first set of reference-associated molecules; etc.); and/or facilitating the characterization of the medical condition based on the at least one abundance metric (e.g., based on the target-associated count ratio and/or the reference-associated count ratio; etc.).

Embodiments of the method 100 and/or system 200 can function to improve accuracy of determining abundance metrics associated with one or more biological targets (e.g., enabling accurate comparisons of abundance measurements for molecules including sequences across multiple loci, such as enabling accuracy associated with coefficient of variation of less than 0.1% and/or any suitable accuracy; etc.). Embodiments of the method 100 and/or system 200 can additionally or alternatively function to leverage the abundance metrics to facilitate characterization (e.g., detect; diagnose; analyze; providing information regarding; provide parameters used in types of characterization such as diagnosis; improve accuracy regarding diagnosis; etc.) and/or facilitate treatment (e.g., through treatment determination, treatment evaluation and modification over time, treatment recommendation, provision, administration, etc.) of one or more conditions (e.g., medical conditions such as one or more chromosomal abnormalities and/or single gene disorders; such as an aneuploidy-associated condition, where characterization can require highly accurate abundance determination; etc.), such as in relation to noninvasive prenatal testing (NIPT).

Embodiments can additionally or alternatively function to detect, quantify, and/or otherwise characterize breakpoints (e.g., quantitatively detecting target sequences including small deletions and/or insertions, such as in relation to detecting beta-thalassemia 619 bp-deletion; such as in relation to NIPT; etc.). In a specific example, the method 100 can include: synthesizing target-associated spike-in molecules including target-associated sequences differing (e.g., by a small number of base pairs) from the target sequences (e.g., a sequence associated with beta-thalassemia 619 bp-deletion; a sequence associated with a different genetic abnormality; etc.) for the biological sample; synthesizing reference-associated spike-in molecules including reference-associated sequences differing (e.g., by a small number of base pairs) from the reference sequences (e.g., a sequence without the beta-thalassemia 619 bp-deletion; a sequence without the genetic abnormality; etc.) for the biological sample; determining abundance ratio metrics respectively for the target (e.g., endogenous to spike-in ratio) and the reference (e.g., endogenous to spike-in ratio), such as through performing processing operations (e.g., amplification, sequencing, etc.) described herein; and/or comparing the abundance ratio metrics for detecting a condition associated with the target (e.g., thalassemia, etc.).

Embodiments can additionally or alternatively function to detect, quantify, and/or otherwise characterize molecules of a particular locus (e.g., for determining an initial abundance metric for a particular locus in a biological sample such as in single-gene NIPT, where the initial abundance metric can be compared to final abundance metrics for evaluating statistical confidence; etc.). In a specific example (e.g., in relation to inheriting sickle cell disease), the method 100 can include: synthesizing target-associated spike-in molecules including target-associated sequences differing (e.g., by a small number of base pairs) from the target sequences (e.g., a sequence at a locus associated with sickle cell disease; a sequence associated with beta-thalassemia 619 bp-deletion; a sequence associated with a different genetic abnormality; etc.) for the biological sample; processing the target-associated spike-in molecules (e.g., of known abundance) with target molecules from a biological sample (e.g., performing amplification, sequencing, etc.); determining one or more abundance metrics for the target (e.g., number of molecules in the biological sample for the target locus, etc.) based on processing the abundance ratio metric (e.g., endogenous to spike-in) with the known abundance metric of the spike-in molecules (e.g., multiplying the abundance ratio by the known number of spike-in molecules); and/or facilitating characterization of the one or more conditions (e.g., status of disease state; etc.) based on processing the one or more abundance metrics with outputs from approaches for determining fetal fraction of molecules (e.g., determining proportion of molecules belonging to mother versus fetus). However, embodiments can include any suitable functionality.

Embodiments of the method 100 and/or system 200 can be used in association with one or more conditions (e.g., in association with characterizing, diagnosing, treating, and/or performing processes related to one or more conditions; etc.), where the conditions can include and/or otherwise be associated with one or more of: NIPT (e.g., in relation to genetic screening for presence of chromosomal abnormalities including aneuploidy, such as trisomy 21 or Down syndrome, trisomy 18 or Edwards syndrome, trisomy 13 or Patau syndrome, sex chromosome aneuploidies such as Turner syndrome, other suitable aneuploidies; chromosomal abnormalities including DiGeorge syndrome; in relation to genetic screening for single gene disorders; rare variant-associated conditions; etc.); other prenatal testing; aneuploidy analysis and/or other suitable analysis outside of a prenatal context; genetic disorders (e.g., single gene disorders including sickle cell disease and/or rare variant-associated conditions; chromosomal abnormalities; disorders associated with gene amplification; gene deletion; partial chromosomal abnormalities; 22q11.2 deletion syndrome or DiGeorge syndrome; Charcot-Marie-Tooth syndrome, cystic fibrosis, Huntington's disease; Duchenne muscular dystrophy; hemophilia, thalassemia; rare variant-associated conditions etc.), other conditions associated with chromosome abnormalities (e.g., additional, missing, irregular chromosomal DNA, etc.), rare variant-associated conditions, cancer (e.g., through analyses associated with any suitable oncogenes, cancer biomarkers, and/or other cancer-associated targets; through analyses associated with liquid biopsies), and/or any other suitable conditions. Conditions can additionally or alternatively include: psychiatric and behavioral conditions (e.g., a psychological disorder; depression; psychosis; etc.); communication-related conditions (e.g., expressive language disorder; stuttering; phonological disorder; autism disorder; voice conditions; hearing conditions; eye conditions; etc.); sleep-related conditions (e.g., insomnia, sleep apnea; etc.); cardiovascular-related conditions (e.g., coronary artery disease; high blood pressure; etc.); metabolic-related conditions (e.g., diabetes, etc.), rheumatoid-related conditions (e.g., arthritis, etc.); weight-related conditions (e.g., obesity, etc.); pain-related conditions; endocrine-related conditions; genetic-related conditions; chronic disease; and/or any other suitable type of conditions.

Embodiments of the method 100 and/or system 200 can additionally or alternatively transform entities (e.g., biological samples, targets, references, synthesized molecules, users, sample handling systems, computational systems, etc.) into different states or things. For example, the method 100 can include synthesizing spike-in molecules (e.g., target-associated molecules, reference-associated molecules) including variation regions to process alongside (e.g., amplify with) target molecules and/or reference molecules for transformation into forms suitable for accurate abundance determination while minimizing amplification bias. Such processes can enable previously unperformable characterizations (e.g., of medical conditions; etc.) and/or treatment evaluations (e.g., through facilitating improved accuracy for meaningful quantification and comparisons of spike-in molecules, target molecules, and/or reference molecules, such as associated with sequences across different loci, etc.). However, portions of embodiments of the method 100 and/or system 200 can provide any other suitable benefits, such as in the context of using non-generalized systems and/or performing unconventional processes.

Sequencing and/or sequencing-related technologies (e.g., in relation to S130 and/or S140) associated with one or more portions of embodiments of the method 100 and/or system 200 can include high throughput sequencing, which can include and/or be associated with any one or more of: NGS, NGS-associated technologies, massively parallel signature sequencing, Polony sequencing, 454 pyrosequencing, Illumina sequencing, SOLiD sequencing, Ion Torrent semiconductor sequencing, DNA nanoball sequencing, Heliscope single molecule sequencing, Single molecule real time (SMRT) sequencing, Nanopore DNA sequencing, any generation number of sequencing technologies (e.g., second-generation sequencing technologies, third-generation sequencing technologies, fourth-generation sequencing technologies, etc.), amplicon-associated sequencing (e.g., targeted amplicon sequencing), metagenome-associated sequencing, sequencing-by-synthesis, tunneling currents sequencing, sequencing by hybridization, mass spectrometry sequencing, microscopy-based techniques, and/or any suitable technologies related to high throughput sequencing. Additionally or alternatively, sequencing and/or sequencing-related technologies can include and/or apply any suitable sequencing technologies (e.g., Sanger sequencing, capillary sequencing, any suitable sequencing technologies, etc.). Additionally or alternatively, any suitable portions of embodiments of the method 100 and/or system 200 can be performed with, include, and/or otherwise be associated with (e.g., generating target-associated molecules and/or reference-associated molecules for; determining abundance metrics based upon corresponding outputs; etc.) any suitable abundance determination techniques (e.g., for measuring relative abundance of different DNA sequences; sequence-specific abundance determination techniques; etc.), including any one or more of: microarrays, fluorescence in situ hybridization (FISH) probes, and/or any suitable techniques. In examples, a large number (and/or any suitable number of spike-ins, such as target-associated molecules and/or reference-associated molecules, can be designed, generated, and/or otherwise processed with single-nucleotide polymorphisms relative to a large number (and/or any suitable number) of target sequences in a way that the polymorphisms can be detected by one or more microarrays. A microarray can then be used to detect the abundance of each spike-in to each target. In a specific example, since all spike-ins can be added at equimolar concentration, any significant differences at different target regions will indicate a difference in abundance of that target region. These differences, aggregated over multiple adjacent target sequences, can then be used to characterize microdeletions, microinsertions, copy number variations, and/or chromosomal abnormalities both for prenatal diagnostics and for liquid biopsies (and/or for any suitable conditions). The aggregation calculations can be performed by any mathematical averaging techniques, including but not limited to local weighting, local regression, Kernel smoothing, and Hidden Markov Models, and/or using any suitable analytical techniques described herein. However, any suitable portions of embodiments of the method 100 and/or system 200 can be performed with, include, and/or otherwise be associated with any suitable abundance determination techniques in any suitable manner.

Additionally or alternatively, data described herein (e.g., abundance metrics; characterizations; models; ratios; identifiers; read depths; sequence reads; molecule designs such as target-associated molecule designs, reference-associated molecule designs, primer designs, experiment designs; etc.) can be associated with any suitable temporal indicators (e.g., seconds, minutes, hours, days, weeks, time periods, time points, timestamps, etc.) including one or more: temporal indicators indicating when the data was collected, determined, transmitted, received, and/or otherwise processed; temporal indicators providing context to content described by the data, such as temporal indicators indicating different stages of spike-in mixture generation and/or suitable sequencing library preparation and/or sequencing; changes in temporal indicators (e.g., data over time; change in data; data patterns; data trends; data extrapolation and/or other prediction; etc.); and/or any other suitable indicators related to time.

Additionally or alternatively, parameters, metrics, inputs, outputs, and/or other suitable data described herein can be associated with value types including any one or more of: scores, binary values, classifications, confidence levels, identifiers (e.g., sample identifiers, molecule identifiers for any suitable molecules described herein, etc.), values along a spectrum, and/or any other suitable types of values. Any suitable types of data described herein can be used as inputs, generated as outputs, and/or manipulated in any suitable manner for any suitable components associated with embodiments of the method 100 and/or system 200.

One or more instances and/or portions of embodiments of the method 100 and/or processes described herein can be performed asynchronously (e.g., sequentially), concurrently (e.g., in parallel; concurrently processing biological samples in a multiplex, automated manner, such as to generated one or more spike-in mixtures; concurrently computationally processing sequence reads to improve system processing ability, such as for determining one or more abundance metrics and/or facilitating one or more characterizations; etc.), in temporal relation to a trigger event, and/or in any other suitable order at any suitable time and frequency by and/or using one or more instances of embodiments of the system 200, components, and/or entities described herein.

Embodiments of the system 200 can include a sample handling network configured to generate molecules (e.g., target-associated molecules, reference-associated molecules), process biological samples, facilitate generation of spike-in mixtures (and/or suitable sequencing libraries; etc.) and/or perform other suitable processes; a sequencing system configured to sequence processed genetic material from spike-in mixtures; a computing system (e.g., remote computing system, local computing system, etc.) configured to analyze the sequences, to determine abundance metrics, to facilitate characterizations, and/or perform suitable computational processes; and/or any other suitable components. However, the method 100 and system 200 can be configured in any suitable manner.

2.1 Generating Target-Associated Molecules.

Embodiments of the method 100 can include generating one or more target-associated molecules S110, which can function to synthesize one or more molecules sharing one or more characteristics (e.g., sequence characteristics, functional characteristics, structural characteristics, evolutionary characteristics, etc.) with one or more targets (e.g., biological targets; etc.), which can facilitate similar sample processing parameters (e.g., amplification parameters, etc.) to reduce bias (e.g., amplification bias, such as through co-amplification with nucleic acid molecules from the biological sample and including one or more target sequence regions of the one or more biological targets, etc.) and to improve accuracy during downstream processing.

Target-associated molecules preferably include target-associated regions (e.g., each target-associated molecule including one or more target-associated regions; etc.). For example, a target-associated molecules can include a target-associated region with sequence similarity (e.g., full sequence similarity; sequence similarity greater than a threshold percentage and/or amount; etc.) to a target sequence region of a biological target associated with the medical condition.

Figure 11:
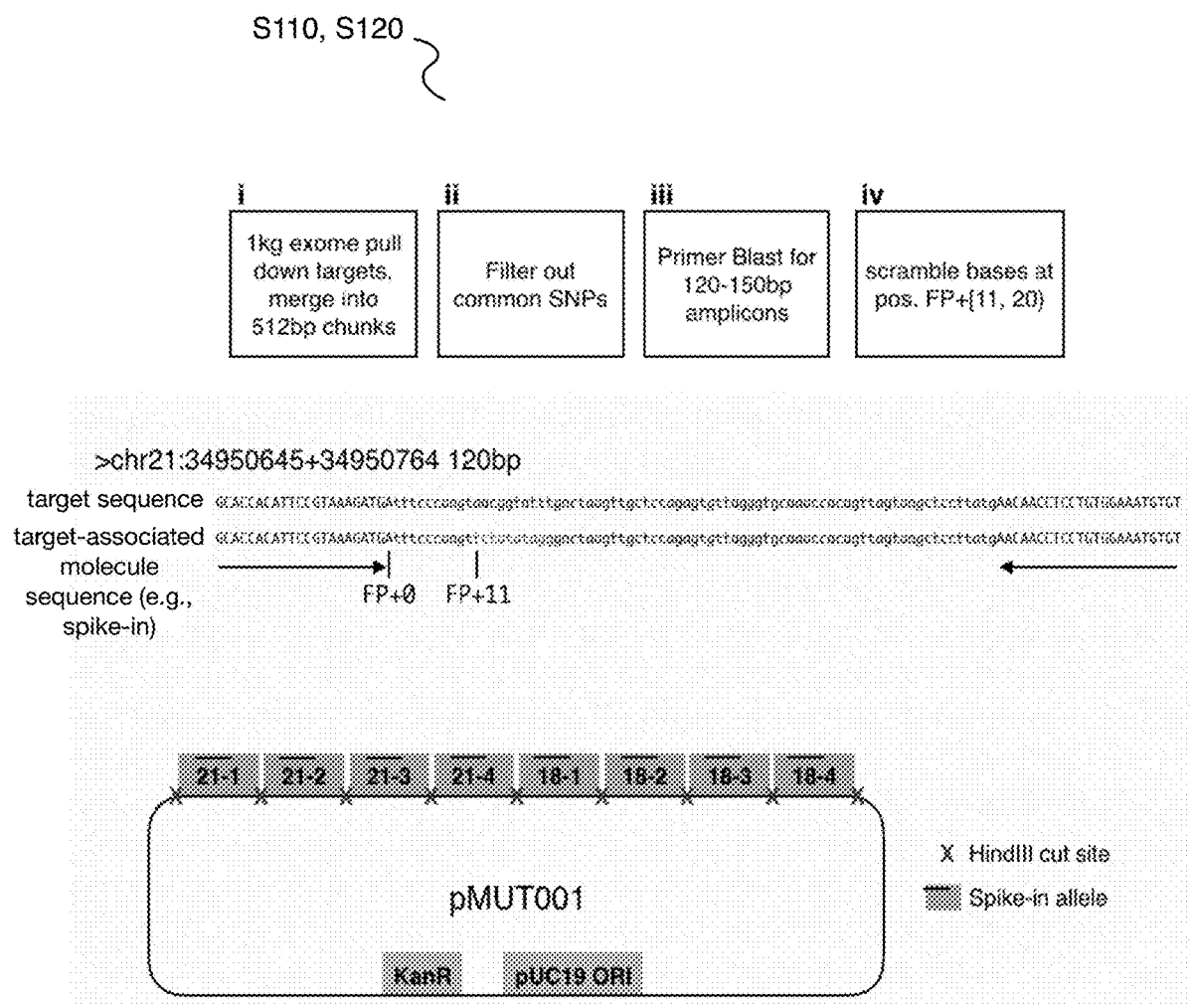
FIG. 11 includes specific examples of determining and generating target-associated molecules and reference-associated molecules (target sequence=SEQ ID NO: 8; target-associated molecule sequence=SEQ ID NO: 9)

Target-associated regions (and/or the target-associated molecules) are preferably associated with (e.g., sharing nucleotide sequences with; sharing sets of bases with a target sequence at corresponding positions; able to be processed with; able to be amplified with, such as through co-amplification; able to be targeted by the same primers; complementary to; targeting; digitally associated with in a computing system; etc.) one or more biological targets and/or target molecules (e.g., target molecules corresponding to biological targets; target molecules including target sequence regions of biological targets; etc.). Biological targets (e.g., target markers; corresponding to, causing, contributing to, therapeutic in relation to, correlated with, and/or otherwise associated with one or more medical conditions; targets of interest; known or identified targets; unknown or previously unidentified targets; etc.) can include any one or more of target sequence regions (e.g., sequences identifying a chromosome; sequences indicative of a condition; sequences that are invariant across a population and/or any suitable set of subjects; conserved sequences; sequences including mutations, polymorphisms; nucleotide sequences; amino acid sequences; etc.), genes (e.g., associated with one or more single gene disorders, etc.), loci, chromosomes (e.g., associated with one or more chromosomal abnormalities; etc.) proteins (e.g., serum proteins, antibodies, etc.), peptides, carbohydrates, lipids, nucleic acids (e.g., extracellular RNA, microRNA, messenger RNA, where abundance determination for RNA targets can include suitable reverse transcriptase operations, etc.), cells (e.g., whole cells, etc.), metabolites, natural products, genetic predisposition biomarkers, diagnostic biomarkers, prognostic biomarkers, predictive biomarkers, other molecular biomarkers, gene expression markers, imaging biomarkers, and/or other suitable targets. Targets are preferably associated with conditions described herein, and can additionally or alternatively be associated with one or more conditions including: symptoms, causes, diseases, disorders, and/or any other suitable aspects associated with conditions. In an example, as shown in FIG. 11, target-associated molecules can include nucleotide sequences identical to one or more regions of a target sequence of a target molecule (e.g., identifying chromosome 21), where primers can concurrently target both the target-associated molecules and the target molecules by targeting the identical regions (e.g., for facilitating co-amplification, such as to reduce amplification bias, etc.). In another example, target-associated molecules can include sequences with any suitable sequence identity to target molecule sequences, where any number and/or type of primers can be used in concurrently or separately targeting the target-associated molecules and target molecules. However, targets (e.g., biological targets, etc.) can be configured in any suitable manner. Additionally or alternatively, target-associated molecules (e.g., target-associated regions of target-associated molecules; etc.) can share any suitable characteristics (e.g., components, etc.) with biological targets (e.g., with target molecules corresponding to biological targets; etc.), such as to facilitate similar sample processing parameters to be able to subsequently generate meaningful comparisons between abundance metrics for the target-associated molecules and the target molecules. However, target-associated molecules can be configured in any suitable manner.

Figure 7A:
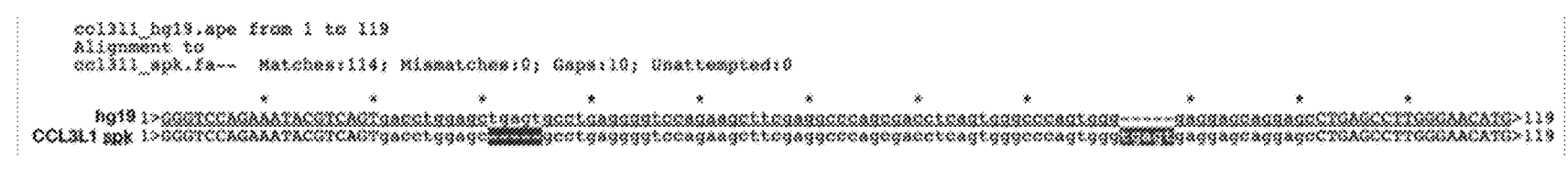
Figure 9A:
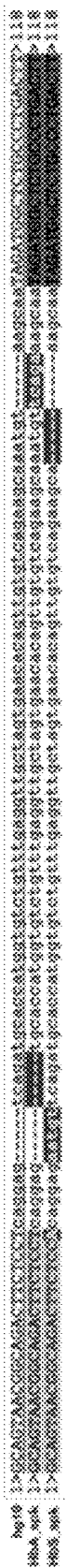
FIGS. 9A-9B include specific examples of target-associated molecules (hg19=SEQ ID NO: 3; HbA_spk=SEQ ID NO: 4; HbS_spk=SEQ ID NO: 5) and applying the target-associated molecules for detecting single nucleotide polymorphisms.

Target-associated molecules preferably include target variation regions (e.g., variation regions of target-associated molecules; each target-associated molecule including one or more variation regions; etc.), where a variation region can include different characteristics from the characteristics of the target molecule. Variation regions preferably include one or more variations (e.g., single nucleotide variations, etc.), such as variations that can enable a corresponding target-associated molecule (e.g., the target-associated molecule including the variation region; etc.) to proceed through sample processing operations in a similar manner to the corresponding target molecules (e.g., nucleic acids including a target sequence region of a biological target; etc.), while facilitating differentiation of the target-associated molecules from the target molecules (e.g., during post-processing of sequence reads for the one or more spike-in mixtures, where sequence reads including the variation region can be mapped to the target-associated molecules as opposed to the biological target; etc.). Such differentiation can facilitate determination of different corresponding abundance metrics that can be meaningful compared (e.g., where the initial abundance, such as the number of molecules and/or concentration, of the set of target-associated molecules can be known prior to generating the spike-in mixture, etc.). In an example, the variation region can include a sequence variation region including a nucleotide sequence differing from a sequence region of the target molecule. In a specific example, as shown in FIGS. 7A and 9A, variation regions can include one or more deletions (e.g., 5-base pair deletion relative a sequence region of "tgagt" of the biological target, as shown in FIG. 7A; 5-base pair deletion relative a sequence region of "aatgt" of the biological target such as HbS, as shown in FIG. 9A; etc.) and/or insertions (e.g., 5-base pair insertion of "tgagt", as shown in FIG. 7A; 5-base pair insertion of "aatgt" relative the biological target such as HbS, as shown in FIG. 9A, etc.) relative to a sequence region (e.g., sequence region of hg19 and/or any suitable genome references, corresponding to CCL3L1, as shown in FIG. 7A; corresponding to hemoglobin, as shown in FIG. 9A; etc.). Variation regions can be designed in coordination with the target-associated regions to facilitate appropriate sequence dissimilarity and sequence similarity, respectively. In a specific example, as shown in FIG. 11, the target-associated molecule can include a nucleotide sequence variation region differing from the corresponding target nucleotide sequence by 10 bases (e.g., where the target sequence includes a "aacggtattt" region (portion of SEQ ID NO: 8) and where the variation region includes a "tctatatagg" region (portion of SEQ ID NO: 9) at corresponding positions, etc.). Sequence variation regions can differ by target sequences by any suitable number and type of bases, at any suitable positions (e.g., sequential positions, non-sequential), across any suitable loci, for any suitable chromosome and/or other target, and/or can differ from target sequences in any suitable manner. Sequence variation regions can include any one or more of substitutions, insertions, deletions, any suitable mutation types, and/or any suitable modifications (e.g., relative one or more sequence regions of a biological target; etc.). For example, target variation regions can include a target variation region including at least one of a first substitution, a first insertion, and a first deletion, relative to the sequence region of the biological target, and reference variation regions can include a reference variation region including at least one of a second substitution, a second insertion, and a second deletion, relative to the sequence region of the biological reference.

Additionally or alternatively, variation regions can include non-sequence variation regions, with functional, structural, evolutionary, and/or other suitable characteristics that are different from the characteristics of the one or more target molecules (e.g., of any suitable type, etc.). However, variation regions can be configured in any suitable manner, and target-associated molecules can include any suitable nucleotide sequence regions.

Figure 7B:
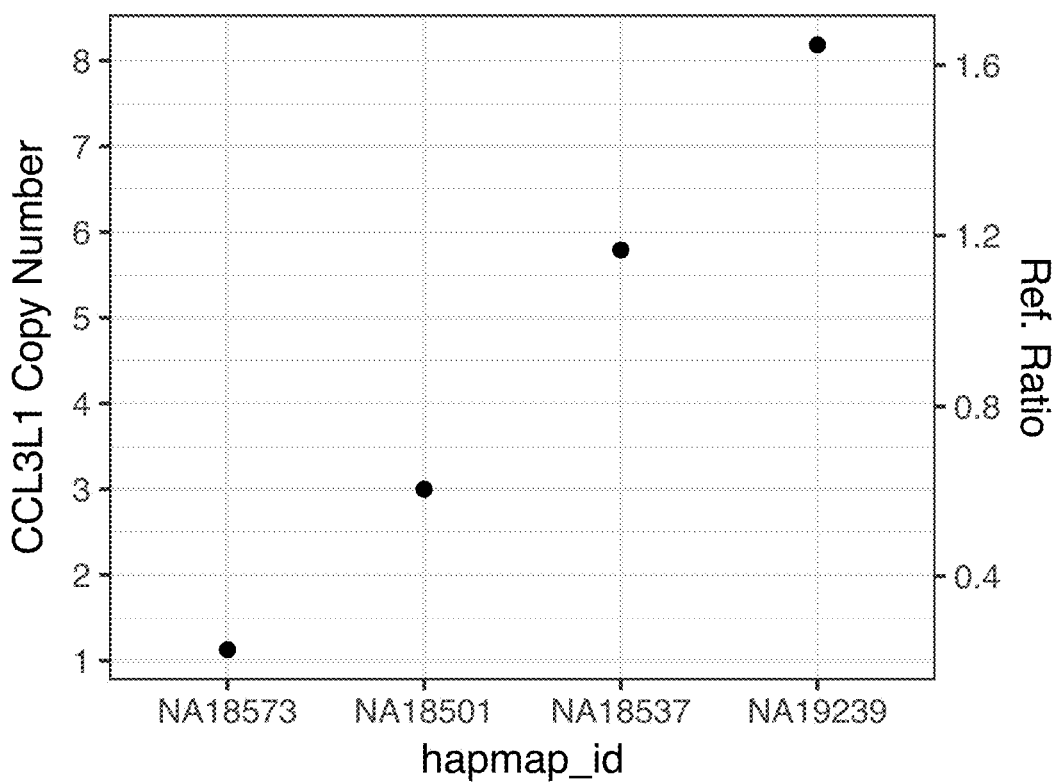

In a specific example, as shown in FIG. 7A, target-associated molecules (e.g., spike-in DNA CCL3L1 gene, etc.) can include a sequence (e.g., including one or more target-associated regions and target variation regions; as shown in the bottom alignment of FIG. 7A; etc.) including engineered indels that enable differentiation between sequencing products derived from human DNA (e.g., from a biological sample, etc.) and target-associated molecules (e.g., synthetic spike-in DNA, etc.), such as where the top alignment, shown in FIG. 7A, is the expected CCL3L1 amplicon after PCR using forward primer=5'-GGGTCCAGAAATACGTCAGT-3' (SEQ ID NO: 16) and reverse primer=5'-CATGTTCCCAAGGCTCAG-3' (SEQ ID NO: 17) based on the hg19 human genome reference assembly. In a specific example (e.g., validating usage of target-associated molecules, such as for characterizing copy number variation; etc.), as shown in FIG. 7B, copy number of CCL3L1 (C-C Motif Chemokine Ligand 3 Like 1) can be measured in HapMap samples using spike-ins, where results can be improved over reported CCL3L1 Copy number measurements assayed by ddPCR (e.g., NA18573=1, NA18501=3, NA18537=6, NA19239=9-10), where 40 ng of genomic DNA can be used in a PCR reaction with PCR primers specific to CCL3L1, and 30,000 copies of CCL3L1 spike-in DNA is added; and after PCR amplification, the "Ref. Ratio" of genomic DNA to spike-in DNA can be measured by DNA sequencing, where NA18501 has been reported to have 3 copies of the CCL3L1 gene, and where CCL3L1 copy number was calculated for NA18573, NA18537, and NA19239 by normalizing their respective Ref. Ratios to the NA18501 Ref. Ratio and multiplying by 3.

In a variation, target-associated molecules can include one or more sequencing molecules (e.g., sequencing regions, etc.) configured to aid in the operation of sequencing systems. Sequencing molecules can include sequencing primers (e.g., Universal PCR primers, Sequencing Primer 1, Sequencing Primer 2 and/or other suitable sequence molecules associated with Illumina sequencing systems), adapter sequences, and/or other suitable components associated with any suitable sequencing systems. Additionally or alternatively, any suitable components described herein (e.g., primer molecules used during amplification operations in generating the spike-in mixture) can include and/or can otherwise be associated with sequencing molecules. However, sequencing molecules can be configured in any suitable manner.

The target-associated molecules (and/or other suitable components described herein, such as reference-associated molecules, components of spike-in mixtures, etc.) can be of any suitable size (e.g., 80-150 base pairs in length, including one or more variation regions of 10 base pairs each or 10 base pairs total; sizes selected based on suitability for different conditions and/or applications described herein; etc.). The set of target-associated molecules can include any number of target-associated molecules associated with any suitable number of targets (e.g., any number of target sequences associated with any number of chromosomes; biological targets; etc.), biological samples (e.g., concurrently synthesizing a batch of molecules for use with samples across multiple users, to improve efficiency of the sample handling system; etc.),conditions (e.g., set of target-associated molecules associated with biological targets associated with different conditions; etc.), and/or other suitable aspects.

In variations, generating target-associated molecules can include generating different types of target-associated molecules (e.g., including different target-associated regions, different variation regions, different sequence molecules, etc.), such as sets of target-associated molecules (e.g., each set corresponding to a different type of target-associated molecules; etc.). Target-associated molecules can include sets of target-associated molecules (e.g., a plurality of different sets, etc.), each set including a different target-associated region associated with (e.g., with sequence similarity to; etc.) a different target sequence region (e.g., different target sequence regions of a same biological target such as a chromosome; different target sequence regions of different biological targets such as different genes; etc.), which can facilitate different pairs of a target-associated region type (e.g., corresponding to a specific target-associated region sequence; etc.) and a target sequence region type (e.g., corresponding to a specific target sequence of a biological target; etc.), such as to determine corresponding abundance metrics such as individual count ratios (e.g., corresponding to the different pairs; such as individual count ratios corresponding to different loci of a chromosome biological target; etc.), which can be used in determining an overall abundance metric with increased accuracy through, for example, averaging and/or performing any suitable combination operations with the individual count ratios.

For example, the method 100 can include generating a first set of target-associated molecules including first target-associated regions with sequence similarity to a first target sequence region of a first biological target; generating a second set of target-associated molecules including second target-associated regions with sequence similarity to a second target sequence region (e.g., of the first biological target; of a second biological target; etc.); determining a first target-associated count ratio associated with the first set of target-associated molecules and the first target sequence region (e.g., ratio of sequence read count for the first set of target-associated molecules and sequence read count for the target molecules including the first target sequence region; etc.); determining a second target-associated count ratio associated with the second set of target-associated molecules and the second target sequence region (e.g., ratio of sequence read count for the second set of target-associated molecules and sequence read count for the target molecules including the second target sequence region; etc.), such as where facilitating characterization of the medical condition can include facilitating characterization of the medical condition based on the first target-associated count ratio and the second target-associated count ratio (and/or one or more reference-associated count ratios.

Figure 12:
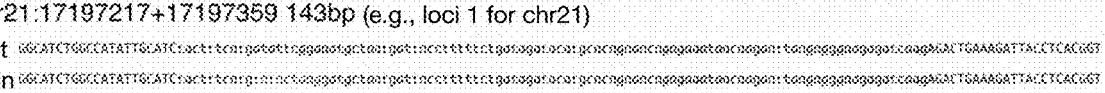
FIG. 12 includes specific examples of target-associated molecules and reference-associated molecules (chr21: 17197217+17197359 Target=SEQ ID NO: 6; chr21: 17197217+17197359 Spike-in=SEQ ID NO: 7; chr21: 34950645+34950764 Target=SEQ ID NO: 8; chr21: 34950645+34950764 Spike-in=SEQ ID NO: 9; chr18: 216483+216603 Target=SEQ ID NO: 10; chr18:216483+ 216603 Spike-in=SEQ ID NO: 11; chr18:74561484+ 74561606 Target=SEQ ID NO: 12; chr18:74561484+ 74561606 Spike-in=SEQ ID NO: 13; chr18:12340277+ 12340405 Target=SEQ ID NO: 14; chr18:12340277+ 12340405 Spike-in=SEQ ID NO: 15).

In a specific example, different sets of target-associated molecules can be associated with different target sequences across different loci. In a specific example, each set can be associated with a different locus for the same chromosome (e.g., a first, second, third, and fourth locus for chromosome 21), where a sequence of a target-associated molecule of a given set can include a sequence region shared by the locus corresponding to the set, and can include a sequence variation region differing (e.g., by 10 bases) from the sequence for the locus. In a specific example, as shown in FIG. 12, a first set of target-associated molecules can be associated with a first locus of chromosome 21, and a second set of target-associated molecules can be associated with a second locus of chromosome 21.

Any number of sets of target-associated molecules and/or any number of types of target-associated molecules can be generated and/or associated with any suitable number of biological targets. In an example, selecting different target-associated molecule sets can be based on accuracy requirements for a given condition and/or application (e.g., selecting a number of sets leading to a corresponding suitable number of individual count ratios to be used in achieving a target accuracy for diagnosing Down syndrome), but can be selected based on any suitable criteria (e.g., parameter to be optimized). However, generating different sets of target-associated molecules can be performed in any suitable manner.

Generating target-associated molecules can include determining target sequence regions (e.g., target sequences, etc.), which can function to select target sequence regions upon which the generation of target-associated molecules can be based. Determining target sequences can be based on: one or more conditions (e.g., selecting target sequences identifying chromosome 21 for facilitating Down syndrome diagnosis, etc.), amplification parameters (e.g., selecting target sequences of a particular length, nucleotide sequence, and/or other parameter for optimizing amplification specificity, such as in relation to primer specificity for the target sequences in relation to PCR amplification, etc.), sequencing parameters (e.g., selecting target sequences for reducing cost, improving accuracy, and/or for other suitable optimizations in relation to sequencing systems and/or operations, etc.), other sample processing parameters, and/or other suitable criteria. In an example, determining target sequences can include computationally searching a database (e.g., DNA database, genome database, gene expression database, phenotype database, RNA database, protein databases, etc.) to generate a target sequence candidate list; and filtering the target sequence candidate list based on criteria described herein, and/or any suitable criteria. In a specific example, as shown in FIG. 11, determining targeting sequences can include extracting a target sequence candidate list (e.g., based on exome pull down; merge into chunks of a suitable number of base pairs; etc.); filtering out candidates including defined types of mutations and/or polymorphisms (e.g., filtering out candidates associated with common single nucleotide polymorphisms to obtain candidates with relative invariance across subjects of a population, etc.); identifying primers for the remaining candidates (e.g., with a Primer-BLAST for 80-150 bp amplicons); and determining candidate regions that are suitable for variation in generating a variation region of target-associated molecule (e.g., through scrambling bases at positions of Forward Primer+[11,20])). However, determining target sequences can be performed in any suitable manner.

Generating the target-associated molecules can include synthesizing the molecules through performing any one or more of: plasmid-based nucleic acid synthesis, other artificial gene synthesis techniques, phosphoramidite approaches, post-synthetic processing, purification (e.g., using high-performance liquid chromatography or other chromatography approaches, desalting, washing, centrifuging, etc.), amplification techniques (e.g., PCR, etc.), tagging techniques (e.g., molecular tagging techniques, fluorescent tagging techniques, particle labeling techniques, etc.), molecule cloning techniques, and/or any suitable sample processing technique.

In variations, generating target-associated molecules can be based on a desired abundance (e.g., determined based on condition, sample, sequencing parameters, sample processing parameters, etc.), such as an abundance ratio (e.g., ratio of target-associated molecule abundance to reference-associated molecule abundance; stoichiometric ratio; concentration ratio; molecule ratio; ratio of any suitable abundance type; etc.). For example, the method 100 can include determining an abundance ratio for the set of target-associated molecules and the set of reference-associated molecules (e.g., based on the medical condition such as a rare variant-associated condition; etc.), generating the set of target-associated molecules based on the abundance ratio (e.g., according to a determined stoichiometric ratio between the target-associated molecules and the reference-associated molecules; etc.); generating the set of reference-associated molecules based on the abundance ratio; and/or determining at least one abundance metric (e.g., associated with the biological target, the set of target-associated molecules, the biological reference, the set of reference-associated molecules, etc.) based on the abundance ratio (and/or sequence reads from sequencing corresponding one or more spike-in mixtures; etc.) and/or any other suitable data. In an example, generating the target-associated molecules can include generating the set of target-associated molecules at a first abundance at least substantially similar (e.g., stoichiometrically equal or substantially equal ratios; substantially similar concentrations; etc.) to a second abundance of the generated set of reference-associated molecules. However, generating target-associated molecules (and/or reference-associated molecules) at desired abundances can be performed in any suitable manner.

Figure 2:
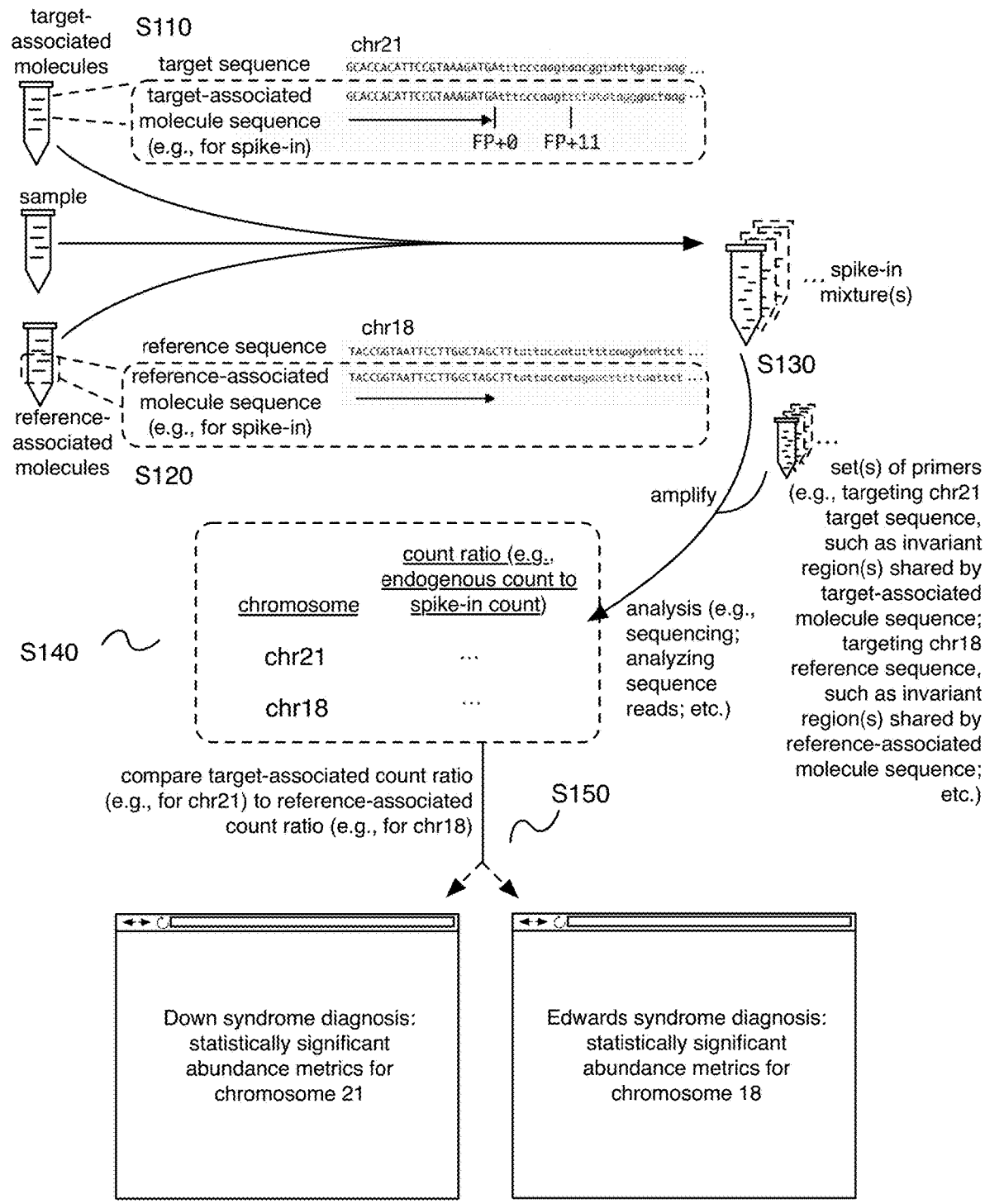
FIG. 2 includes a schematic representation (chr 21 target sequence=portion of SEQ ID NO: 8; chr 21 target-associated molecule sequence=portion of SEQ ID NO: 9; chr 18 reference sequence=portion of SEQ ID NO: 10; chr 18 reference-associated molecule sequence=portion of SEQ ID NO: 11) of a variation of an embodiment of a method.
Figure 3:
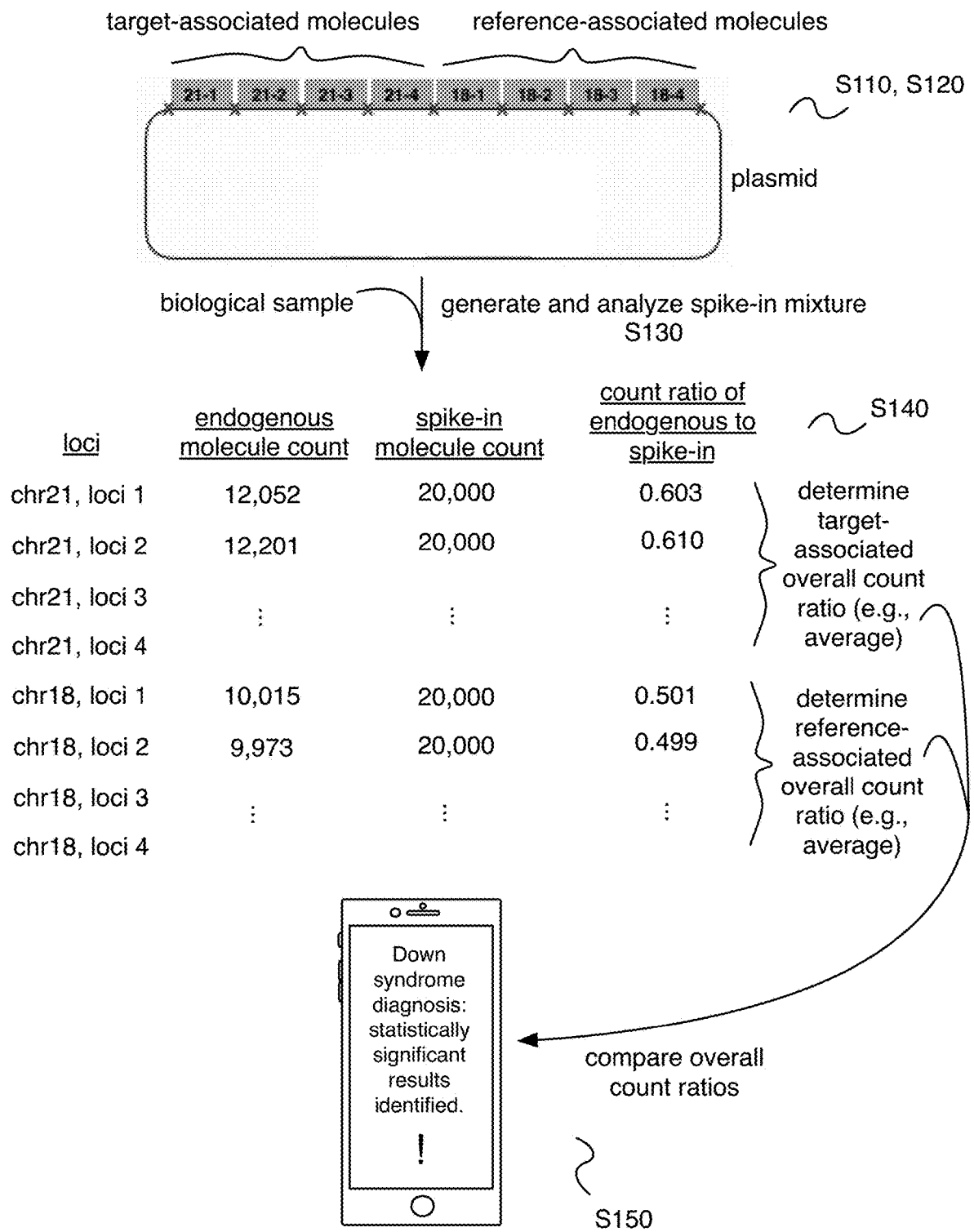
FIG. 3 includes a schematic representation of a variation of an embodiment of a method.
Figure 8:
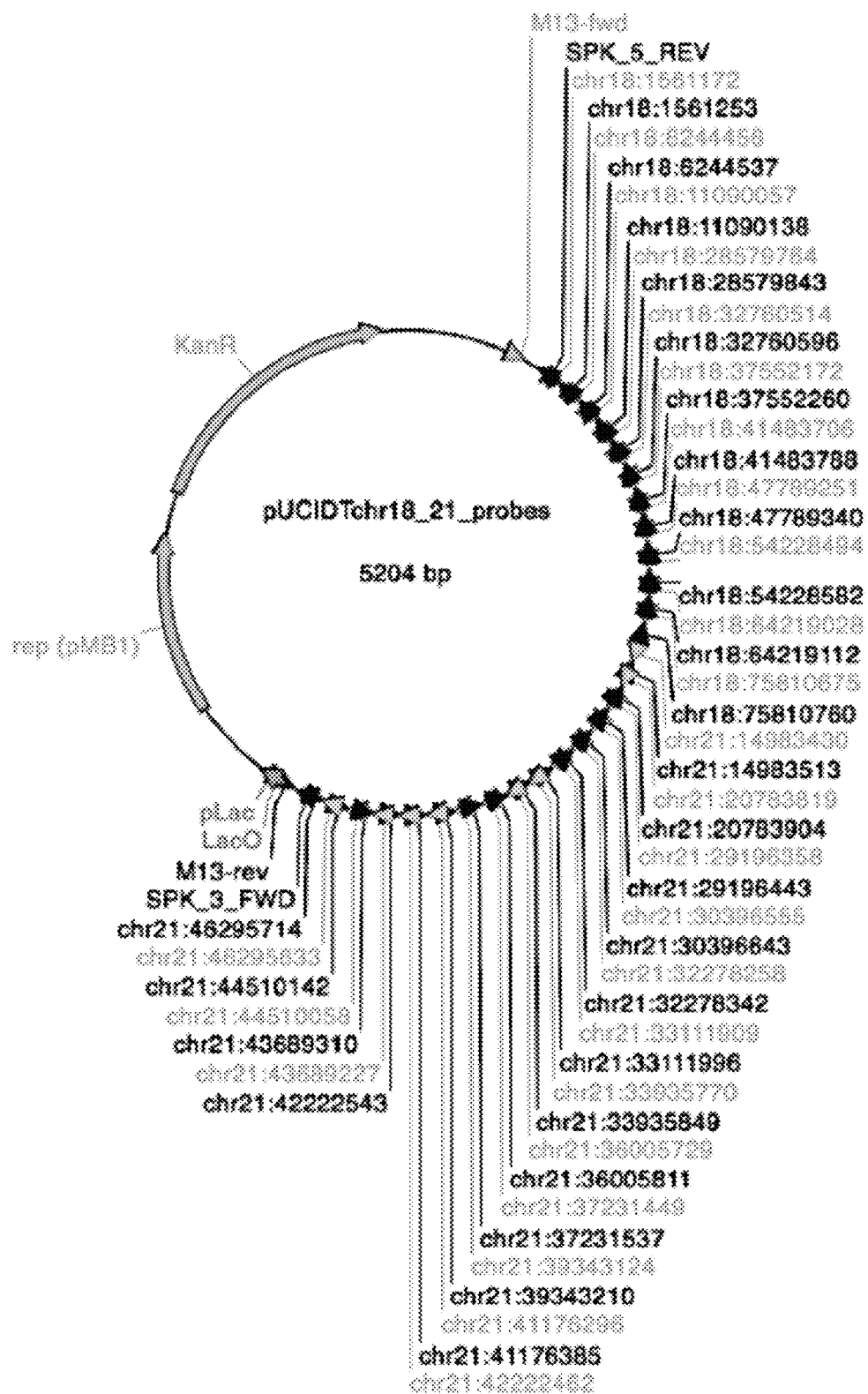
FIG. 8 includes a specific example of a plasmid.

In a variation, as shown in FIGS. 8 and 11, synthesizing the molecules can include generating one or more plasmids. The plasmids preferably include the one or more target-associated molecules (e.g., target-associated regions of target-associated molecules; variation regions of target-associated molecules; any suitable regions of target-associated molecules; etc.) and/or the one or more reference-associated molecules (e.g., any suitable regions of reference-associated molecules; etc.), where including both the target-associated molecules and the reference-associated molecules can facilitate generation of target-associated molecules and reference-associated molecules of same or substantially similar abundance (e.g., same molar ratios) such as for use in generating one or more spike-in mixtures. In an example, as shown in FIGS. 2 and 3, the method 100 can include generating a plasmid including: different types of target-associated molecules (e.g., each type corresponding to a different loci for chromosome 21, etc.) and different types of reference-associated molecules (e.g., each type corresponding to a different loci for chromosome 18, etc.). In an example (e.g., such as where a set of target-associated molecules is generated at a first abundance at least substantially similar to a second abundance of a generated set of reference-associated molecules; etc.), the method 100 can include generating at least one plasmid including target-associated regions (e.g., of target-associated molecules; etc.), target variation regions (e.g., of target-associated molecules; etc.), reference-associated regions (e.g., of reference-associated molecules; etc.), and reference variation regions (e.g., of reference-associated molecules; etc.), generating the set of target-associated molecules (e.g., at the first abundance; etc.) based on processing of the at least one plasmid; and/or generating the set of reference-associated molecules (e.g., at the second abundance; etc.) based on the processing of the at least one plasmid.

Additionally or alternatively, the plasmids can include one or more: cut sites (e.g., HindIII, EcoRI, XhoI, BamHI, PstI, etc.), origin of replication sites (e.g., pUC19 ORI, other pUC sites, etc.), multiple cloning sites, selectable markers (e.g. KanR for kanamycin resistance; resistance associated with ampicillin, chloramphenicol, tetracycline; etc.), reporter markers, backbone, and/or any suitable components. The plasmids can be of any suitable length (e.g., fewer than 10 kilobases; greater than 10 kilobases; etc.), and different sets of target-associated molecules and/or reference-associated molecules can be distributed across different plasmids in any suitable manner (e.g., a first plasmid including the different sets of target-associated molecules; a second plasmid including the different sets of reference-associated molecules; etc.). However, leveraging plasmids and/or other suitable techniques to generate any suitable components (e.g., at any suitable abundance) described herein can be performed in any suitable manner. Additionally or alternatively, any suitable number of molecules and/or types of molecules can be generated at any suitable time and frequency. However, generating target-associated molecules S110 can be performed in any suitable manner.

2.2 Generating Reference-Associated Molecules.

Embodiments of the method 100 can include generating one or more reference-associated molecules S120, which can function to synthesize one or more molecules sharing one or more characteristics with one or more biological references (e.g., reference molecules corresponding to the one or more biological references; etc.), which can facilitate similar amplification parameters and/or other sample processing parameters during processing of the reference-associated molecules and reference molecules (e.g., nucleic acids including one or more reference sequence regions; etc.). Reference-associated molecules are preferably associated with one or more references (e.g., biological references, etc.), such as references facilitating abundance metric comparisons to abundance metrics for target molecules and/or target-associated molecules (e.g., comparisons between reference-associated count ratios and target-associated count ratios; etc.). For example, as shown in FIG. 12, the set of reference-associated molecules can be associated with a chromosomal biological reference (e.g., chromosome 18).

Reference-associated molecules can include any one or more of reference-associated regions (e.g., with sequence similarity to a reference sequence region of a biological reference; etc.); reference variation regions (e.g., variation regions of reference-associated molecules; with sequence dissimilarity to a sequence region of the biological reference; etc.); sequencing molecules; and/or any other suitable regions. In a specific example, reference-associated molecules can include nucleotide sequences shared with reference sequence regions, and can include a sequence variation region differing from the reference sequence (e.g., by 10 base pairs). Additionally or alternatively, references (e.g., biological references; etc.) can include any suitable targets (e.g., biological targets; described herein; etc.); can be associated with any suitable biological targets (e.g., wildtype version of a mutation associated with a biological target; etc.); and/or can include any suitable similarity and/or difference from targets.

In a variation, generating the reference-associated molecules can include selecting reference sequences associated with one or more conditions (e.g., a different condition from a condition associated with the target sequences), which can enable concurrent screening of a plurality of conditions (e.g., through performing a single instance of an embodiment of the method 100; through performing any suitable portions of embodiments of the method 100). In a specific example, the method 100 can include selecting target sequences identifying a first chromosome (e.g., chromosome 21 for characterizing trisomy 21, etc.); and selecting reference sequences identifying a second chromosome (e.g., chromosome 18 for characterizing trisomy 18, etc.). Additionally or alternatively, applying embodiments of the method 100 to characterize and/or treat multiple conditions can be performed in any suitable manner.

Figure 9B:
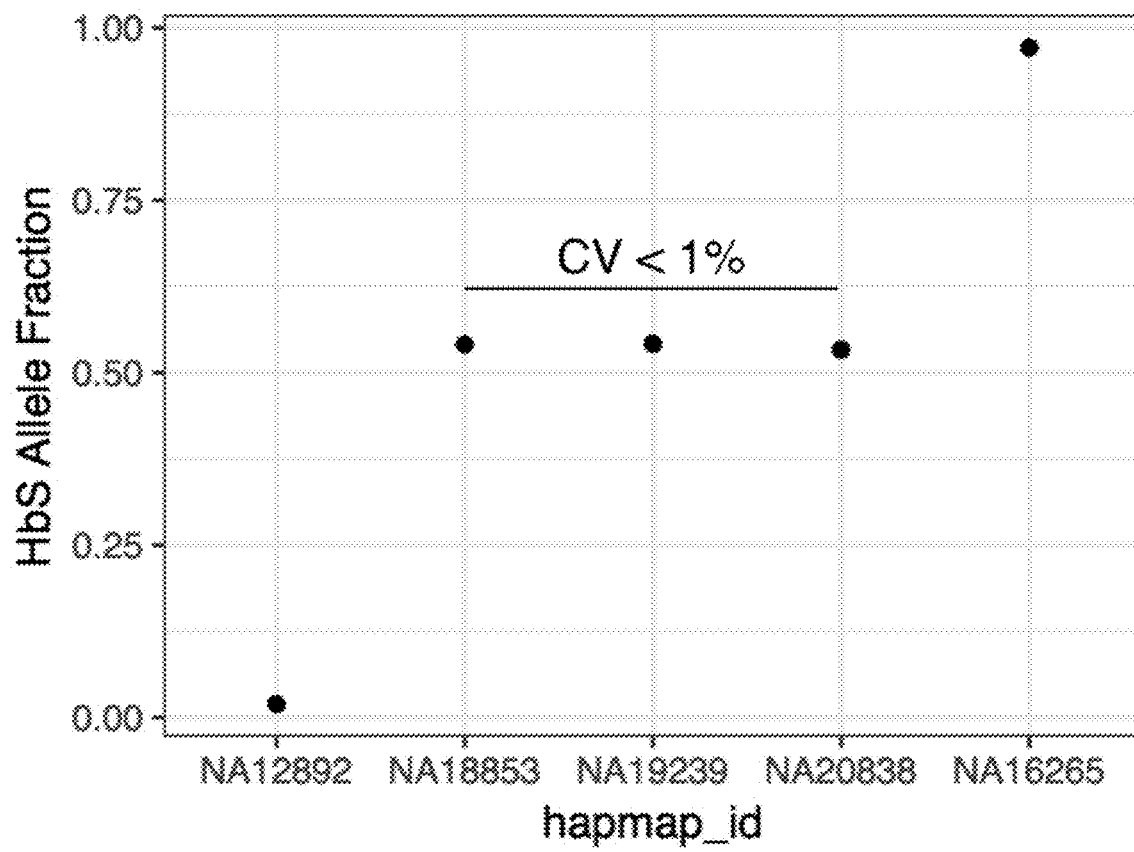

Reference-associated molecules can be configured in any suitable manner analogous to target-associated molecules (e.g., any suitable size, type, regions, such as analogous to size, type, regions of target-associated region; etc.). In an example, example, as shown in FIG. 9A, a reference-associated molecule can include one or more reference-associated regions with sequence similarity to a reference sequence region (e.g., of a biological reference, such as HbA; etc.); and one or more reference variation regions with sequence dissimilarity to a sequence region (e.g., of the biological reference; a 5-base pair deletion relative the sequence region, as shown in FIG. 9A; a 5-base pair insertion such as "tcaga" relative the sequence region, as shown in FIG. 9A; etc.). In a specific example, as shown in FIG. 9A, reference-associated molecules (e.g., "HbA_spk"; HbA spike-in DNA; etc.) can include a sequence including one or more reference-associated regions and reference variation regions (e.g., as shown in the middle alignment of FIG. 9A; etc.), where the top alignment is the expected HBB (hemoglobin beta) amplicon after PCR using forward primer=5'-GCAGTAACGGCAGACTTCTCCA-3' (SEQ ID NO: 18) and reverse primer=5'-AAGTCAGGGCAGAGC-CATCTA-3' (SEQ ID NO: 19) based on the hg19 human genome reference assembly, and where the bottom alignment includes a sequence of target-associated molecules (e.g., "HbS_spk"; HbS spike-in DNA; etc.) respectively, and where PCR primers can include a phosphorothioate bond at 3' terminal nucleotide bond. In a specific example (e.g., validating usage of target-associated molecules and/or reference-associated molecules, such as for single gene disorders and/or rare variant-conditions, such as for detecting single nucleotide polymorphisms (SNPs); etc.), as shown in FIG. 9B, measurement of HbS allele fraction from NA12892 (HbAA), NA18853 (HbAS), NA19239 (HbAS), and NA16265 HbSS) can be used to illustrate application of target-associated molecules and/or reference-associated molecules. However, reference-associated molecules can be configured in any suitable manner.

Generating reference-associated molecules S120 can be performed in any suitable manner analogous to generating target-associated molecules S110 (e.g., generating reference-associated molecules including reference-associated regions and/or reference variation regions in a manner analogous to generating target-associated molecules including target-associated regions and/or target variation regions; determining reference sequences; synthesizing using any suitable sample processing technique, synthesizing using plasmids; etc.), and/or can be performed in any suitable manner.

2.3 Facilitating Generation of a Spike-In Mixture.

Embodiments of the method 100 can include facilitating generation of one or more spike-in mixtures S130 (e.g., based on processing the set of target-associated molecules and the set of reference-associated molecules with one or more biological samples from a user, etc.), which can function to amplify (e.g., under similar amplification parameters), perform pre-processing upon (e.g., sample preparation, lysis, bead-based processes, other purification and/or nucleic acid extraction techniques, etc.), and/or otherwise process the target-associated molecules, reference-associated molecules, components of the biological sample (e.g., nucleic acid molecules; etc.), and/or other suitable components into a form (e.g., one or more mixtures; etc.) suitable for subsequent analysis (e.g., sequencing; etc.) and/or abundance metric determination.

Facilitating generation of the spike-in mixtures can include any one or more of: preparing and/or providing components for generation of the spike-in mixtures (e.g., providing one or more sets of target-associated molecules and/or one or more sets of reference-associated molecules to an entity for generation by the entity of the at least one spike-in mixtures with a biological sample obtained by the entity; etc.); generating the spike-in mixtures (e.g., performing the actual generation of the spike-in mixtures; etc.); guiding (e.g., instructing; etc.) one or more entities in generation of the one or more spike-in mixtures;) and/or performing any suitable processes for facilitating generation of the one or more spike-in mixtures.

Collected biological samples (e.g., collected using sample containers provided to users in sample collection kits; collected by other entities generating the spike-in mixtures; etc.) can include any one or more of: blood, plasma, serum, tissue, biopsies, sweat, urine, feces, semen, vaginal discharges, tears, interstitial fluid, other body fluid, and/or any other suitable samples (e.g., associated with a human user, animal, object such as food, microorganisms, etc.). In examples, such as for NIPT, biological samples can include one or more maternal samples. Biological samples preferably include target molecules (e.g., nucleic acid molecules including one or more target sequence regions; etc.) and/or reference molecules (e.g., nucleic acid molecules including one or more reference sequence regions; etc.), such as where the target molecules can be amplified with the target-associated molecules under similar parameters; where the reference molecules can be amplified with the reference-associated molecules under similar parameters; etc.). Additionally or alternatively, biological samples can include components from multiple users (e.g., a blood sample including nucleic acids from a mother and nucleic acids from the mother's unborn baby, where the nucleic acid mixture can be indicative of an abnormal abundance of chromosome 18, etc.), components collected across multiple time periods, and/or components varying across any suitable condition, such that generating spike-in mixture(s) can be performed for any suitable number and type of entities.

Facilitating generation of one or more spike-in mixtures preferably includes combining target-associated molecules with one or more target molecules from the biological sample (and/or combining target-associated molecules with molecules potentially including target sequence regions, such as where a biological sample may lack target molecules and/or associated target sequence regions; etc.); and/or combining reference-associated molecules with one or more reference molecules from the biological sample. Combining can include one or more of: combining each of the molecules into a single mixture (e.g., including the target-associated molecules, target molecules, reference-associated molecules, reference molecules; etc.); subsampling a biological sample (e.g., a pre-processed sample) for a first and a second mixture, where target-associated molecules can be spiked into the first mixture (e.g., which includes target molecules), and reference-associated molecules can be spiked into the second mixture (e.g., which includes reference molecules); subsampling the pre-processed biological sample into a plurality of mixtures, each corresponding to a different set of target-associated molecules (e.g., corresponding to different target loci for a target chromosome, etc.) and/or a different set of reference-associated molecules (e.g., corresponding to different loci for a reference chromosome, etc.); and/or any other suitable approach to combining the molecules. Additionally or alternatively, separate mixtures can be generated for each type of molecule (e.g., without combining different types of molecules). Combining molecules preferably includes using an abundance of target-associated molecules that is the same or substantially similar to the abundance of reference-associated molecules. Further, combining molecules preferably includes using the same or substantially similar abundances across different sets of target-associated molecules (e.g., associated with different loci), and across different sets of reference-associated molecules. Alternatively, any suitable abundances for different molecule types can be used.

In a variation, combining molecules can include modifying (e.g., during pre-processing) abundances of the target-associated molecules, the reference-associated molecules, and/or other suitable components. For example, modifying abundances can be based on one or more desired abundances (e.g., a desired abundance ratio, such as determined based on a medical condition, associated probabilities, etc.). For example, modifying abundances of molecules can include measuring initial abundances of the molecules (e.g., abundance of the target-associated or reference-associated DNA molecules extracted from plasmid-based synthesis); and modifying the abundances (e.g., through dilution, amplification, etc.) based on expected abundances of target molecules and/or reference molecules (e.g., expected count for endogenous target molecules and endogenous reference molecules in the biological sample, etc.). In another variation, generating spike-in mixtures can omit modification (e.g., during pre-processing) of abundances (e.g., where the abundance results for a first instance of an embodiment of the method 100 can be used in determining a correction factor to be used in subsequent instances of the embodiment of the method 100; etc.). However, combining molecules can be performed in any suitable manner.

Generating the spike-in mixture preferably includes amplifying (e.g., co-amplifying, etc.) the target-associated molecules with the target molecules, and amplifying (e.g., co-amplifying, etc.) the reference-associated molecules with the reference molecules. Amplification can include performing any one or more of: PCR-based techniques (e.g., solid-phase PCR, RT-PCR, qPCR, multiplex PCR, touchdown PCR, nanoPCR, nested PCR, hot start PCR, etc.), helicase-dependent amplification (HDA), loop mediated isothermal amplification (LAMP), self-sustained sequence replication (3SR), nucleic acid sequence based amplification (NASBA), strand displacement amplification (SDA), rolling circle amplification (RCA), ligase chain reaction (LCR), and/or any other suitable amplification techniques and/or associated protocols (e.g., protocols for minimizing amplification bottlenecking). In an example, generating a spike-in mixture can include performing a plurality of PCR rounds to amplify the target-associated molecules with the target molecules (e.g., using primers targeting a sequence shared by both the target-associated molecules and the target molecules), and to amplify the reference-associated molecules with the reference molecules (e.g., using primers targeting a sequence shared by both the reference-associated molecules and the reference molecules). In a specific example, the amount of amplification (e.g., number of PCR rounds, cycles, etc.) can be performed according to results of validation experiments (e.g., during primer selection and validation, stopping PCR reactions at different amplification cycles and visualizing products by gel electrophoresis to determine adequacy of amplification for conditions and/or applications described herein, such as sufficient amplification for next-gen sequencing while minimizing saturation to facilitate preservation of ratios; etc.). In specific examples, generating spike-in mixtures can include subsampling the biological sample into different subsamples designated for different pairs of a target molecule type (or reference molecule type) and a target-associated molecule type (or reference-associated molecule type), each pair corresponding to a different loci (e.g., of chromosome 21 or chromosome 18, etc.) and/or different target; and amplifying the different subsamples (e.g., through sets of PCR rounds) by using primers specific to the pair corresponding to the subsample. Additionally or alternatively, target molecules and target-associated molecules for multiple pairs of a target molecule type (e.g., associated with a plurality of different targets, etc.) may be amplified in the same tube (and/or any suitable number of tubes), such as through multiplex PCR, which can facilitate conserving a precious sample; an amplified target molecule and target-associated molecule pair may then be selectively sequenced via a sequencing oligonucleotide that is specific to the target pair. In this or other examples, subsampling and/or other sample modification operations can be performed in any suitable order.

Figure 10:
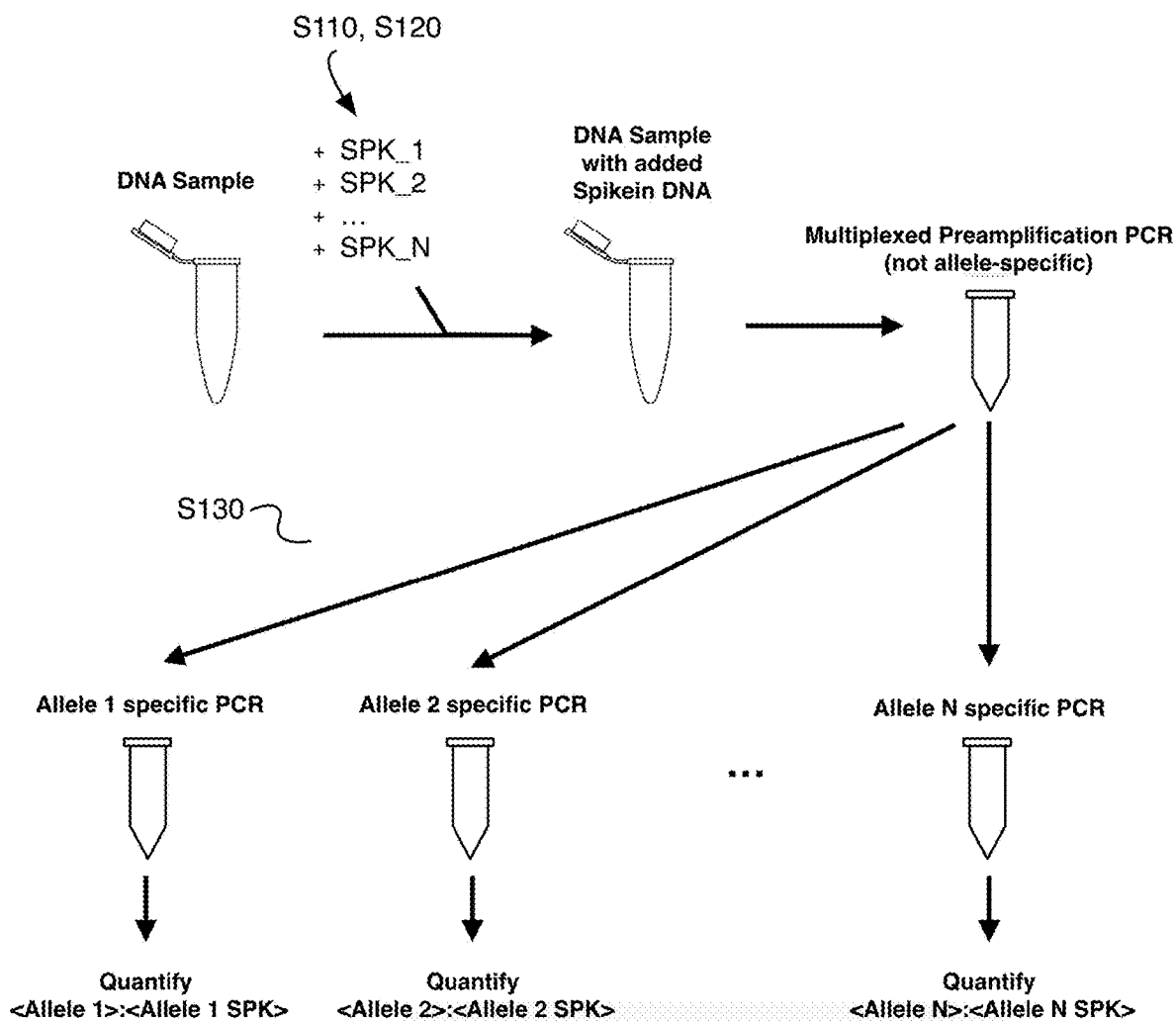
FIG. 10 includes a schematic representation of facilitating characterization associated with a plurality of targets, in a variation of an embodiment of a method.

In variations, as shown in FIG. 10, generation of spike-in mixtures can be associated with (e.g., tailored for, adapted to; etc.) a plurality of target sequence regions (e.g., corresponding to a large number of target sequence regions; a large number of biological targets; etc.). For example, a target sequence region can be from a set of target sequence regions; a set of target-associated molecules can be from sets of target-associated molecules (e.g., different sets of target-associated molecules; etc.) associated with different target sequence regions from the set of target sequence regions, where generation of at least one spike-in mixture can include preamplification with the biological sample based on a set of non-specific primers, to generate a pre-amplified sample; and/or subsampling of the pre-amplified sample to facilitate target sequence region-specific co-amplification based on sets of specific primers associated with the set of target sequence regions and the sets of target-associated molecules (e.g., where different sets of primer types can be used for different co-amplification operations between different target sequence regions and different corresponding sets of target-associated molecules; etc.). For example, as shown in FIG. 10, optional preamplification PCR that is not allele-specific can be performed before dividing the resultant pre-amplified DNA (e.g., including components of the biological sample; target-associated molecules; reference-associated molecules; etc.) into multiple downstream allele-specific PCRs (e.g., for facilitating co-amplification; for facilitating amplification bias reduction; etc.), such as by designing and/or applying PCR primers that are outside the one or more target polymorphisms, where the preamplification PCR can include multiplex PCR using multiple primer pairs if multiple alleles spanning multiple loci are to be measured, and where pre-amplification can enable the pre-amplified product to be allocated into multiple subsequent allele-specific PCR reactions without diluting out rare variants (e.g., in relation to characterization of one or more rare variant-associated conditions; etc.). In examples, target-associated molecules and/or reference-associated molecules (e.g., spike-in DNA, etc.) can be added either before pre-amplification PCR (e.g., as shown in FIG. 10), and/or the target-associated molecules and/or reference-associated molecules spike-in DNA can be added after pre-amplification and before sample division into allele-specific PCR. However addition of target-associated molecules and/or reference-associated molecules (e.g., in relation to different portions of generation of one or more spike-in mixtures; etc.) can be performed at any suitable time and frequency. Additionally or alternatively, any suitable sample processing operations can be performed in any suitable sequence and/or frequency for facilitating generation of one or more spike-in mixtures.

Additionally or alternatively, target molecules can be amplified independently from the target-associated molecules, and reference molecules can be amplified independently from reference-associated molecules. However, amplifying molecules in relation to generating one or more spike-in mixtures can be performed in any suitable manner (e.g., where primers can be configured in any suitable manner, etc.), and generating one or more spike-in mixtures S130 can be performed in any suitable manner.

2.4 Determining an Abundance Metric.

Embodiments of the method 100 can include determining an abundance metric S140 (e.g., for one or more biological targets based on an analysis of the one or more spike-in mixtures, etc.), which can function to accurately determine abundance metrics (e.g., count metrics such as sequence read count, absolute molecule count, etc.) such as for use in characterizing one or more conditions (e.g., based on comparison of abundance metrics; based on abundance metrics that can be compared across target-associated molecules, reference-associated molecules, biological targets, biological references; such as for detecting an elevated abundance of chromosome 21 in relation to a reference chromosome in a blood sample of a pregnant female, etc.). Analyses of one or more spike-in mixtures (e.g., for facilitating determination of one or more abundance metrics; etc.) can include one or more of: sequencing of the spike-in mixture (and/or a processed form of the spike-in mixture), such as using any suitable sequencing technologies (e.g., described herein, etc.); computationally processing the sequence read results (e.g., mapping sequence reads to sequences associated with target molecules, target-associated molecules, reference molecules, reference-associated molecules, and/or other suitable molecules, to determine corresponding abundances); and/or any other suitable processes. Computational processing (e.g., of the sequence reads results; etc.), determining abundance metrics, facilitating characterization of one or more conditions, and/or suitable portions of embodiments of the method 100 (e.g., facilitating treatment, etc.) can include any one or more of: performing pattern recognition on data, performing statistical estimation on data (e.g. ordinary least squares regression, non-negative least squares regression, principal components analysis, ridge regression, etc.), fusing data from multiple sources, combination of values (e.g., averaging values, etc.), compression, conversion (e.g., digital-to-analog conversion, analog-to-digital conversion), wave modulation, normalization, deconvolving (e.g., Fourier deconvolution; Gaussian function-based deconvolution; Lucy-Richardson deconvolution etc.), extracting features, updating, ranking, validating, filtering (e.g., for baseline correction, data cropping, etc.), noise reduction, smoothing, filling (e.g., gap filling), aligning, model fitting, windowing, clipping, transformations, mathematical operations (e.g., derivatives, moving averages, summing, subtracting, multiplying, dividing, etc.), multiplexing, demultiplexing, interpolating, extrapolating, clustering, other signal processing operations, other image processing operations, visualizing, and/or any other suitable processing operations.

Abundance metrics can include any one or more of counts (e.g., sequence read count; absolute molecule count; counts of target-associated molecules; counts for biological targets, such as for target molecules corresponding to the biological targets; counts for reference-associated molecules; counts for biological references, such as for reference molecules corresponding to the biological references; etc.); ratios (e.g., a target-associated count ratio of a count for a biological target to a count for target-associated molecules; a reference-associated count ratio of a count for a biological reference to a count for reference-associated molecules; ratios with any suitable numerator and denominator associated with counts and/or other suitable abundance metrics; etc.); individual abundance metrics (e.g., individual abundance metrics such as individual counts for pairs of target-associated region type and target sequence region type; individual counts for individual samples; individual abundance metrics such as individual counts for different types of molecules, targets, references, described herein; etc.); overall abundance metrics (e.g., based on individual abundance metrics; overall target-associated count ratios; overall reference-associated count ratios; etc.); relative abundances; absolute abundances; and/or other suitable abundance metrics. Abundance metrics associated with target molecules and/or biological targets (e.g., a target-associated count ratio) can preferably be compared to abundance metrics associated with reference molecules and/or biological references (e.g., a reference-associated count ratio), which can facilitate relative abundance analyses (e.g., in screening for conditions associated with aneuploidy; for suitable comparisons usable in characterization of one or more conditions; etc.).

In a variation, determining an abundance metric can include determining an overall count ratio from a plurality of individual count ratios, which can increase the accuracy of the count ratio. For example, as shown in FIG. 3, determining abundance metrics can include determining an overall target-associated count ratio from averaging individual count ratios calculated for different pairs of target-associated molecule type and target sequence region type (e.g., corresponding to different loci of a target chromosome) (and/or target molecule type, biological target type, etc.); determining an overall reference-associated count ratio from averaging individual count ratios calculated for different pairs of reference-associated molecule type and reference sequence region type (e.g., corresponding to different loci of a reference chromosome) (and/or reference molecule type, biological reference type, etc.); and/or comparing the overall target-associated count ratio to the overall reference-associated count ratio (e.g., in facilitating characterization of one or more conditions, etc.). For example determining an overall target-associated count ratio can be based on combination of a first target-associated count ratio (e.g., determined based on a count for first target-associated molecules and a count for first target molecules including a first target sequence region; etc.) and a second target-associated count ratio (e.g., determined based on a count for second target-associated molecules and a count for second target molecules including a second target sequence region; etc.), such as where facilitating characterization of the medical condition can based on the overall target-associated count ratio (and/or one or more reference-associated count ratios, such as one or more overall reference-associated count ratios; etc.).

Additionally or alternatively, determining overall abundance metrics from individual abundance metrics (and/or suitable portions of embodiments of the method 100) can leverage any suitable statistical approach (e.g., averaging, median, etc.), and/or can be performed in any suitable manner. In another variation, abundance metrics can be determined over time (e.g., for different biological samples collected over time; by performing multiple instances of embodiments of the method 100 over time; etc.), such as where the series of abundance metrics can be analyzed in facilitating characterizations of one or more conditions (e.g., monitoring chromosome 21 abundance over different stages of the pregnancy, and processing the set of data to diagnose Down syndrome; etc.), treatments, and/or other suitable information. In another variation, determining an abundance metric can include applying an abundance determination model including any one or more of: probabilistic properties, heuristic properties, deterministic properties, and/or any other suitable properties. Additionally or alternatively, determining overall abundance metrics can be performed in any suitable manner. However, determining abundance metrics S140 can be performed in any suitable manner.

2.5 Facilitating Characterization of a Condition.

Embodiments of the method 100 can include facilitating characterization of one or more conditions S150 (e.g., medical conditions such as genetic disorders; based on one or more abundance metric; etc.), which can function to detect, diagnose, analyze, determine characterizations for, aid one or more care providers in relation to, provide data (e.g., parameters; etc.) regarding; and/or otherwise facilitate characterization of one or more conditions. Characterizations can include any one or more of: diagnoses, risk assessments, causes (e.g., identification of user behaviors, demographics, medical history, genetics, and/or other suitable aspects contributing to the condition), and/or other suitable information informative of the one or more conditions. In variations, one or more characterizations can be used in any one or more of: determining a treatment, informing users, informing care providers (e.g., guiding care provider in diagnoses; etc.), and/or performing any suitable operations. Facilitating one or more characterizations is preferably based on comparisons of count ratios (e.g., a comparison of a target-associated count ratio against a reference-associated count ratios), but can additionally or alternatively be based on any number and/or type of abundance metrics (e.g., any suitable analytical techniques applied to the abundance metrics; etc.). In an example, as shown in FIG. 2, a comparison between a count ratio for chromosome 21 and a count ratio for chromosome 18 (e.g., for a biological sample from a pregnant female) can indicate outcomes of: elevated relative abundance of chromosome 21 (e.g., with statistical significance indicating diagnosis of Down syndrome), an elevated relative abundance of chromosome 18 (e.g., with statistical significance indicating diagnosis of Edwards syndrome), no elevation of either chromosome, and/or other suitable outcomes. In an example, the method 100 can include determining abundance metrics for a first population of subjects exhibiting the condition and for a second population of subjects not exhibiting the condition; determining a set of reference abundance metrics (e.g., for a reference model, such as a machine learning model, generated with the abundance metrics and supplementary features regarding the populations of subjects) based on the abundance metrics; and facilitating characterization of a condition for a current subject based on comparing abundance metrics for the subject to the reference abundance metrics (e.g., inputting the subject's abundance metrics and associated supplementary features regarding the subject into the reference model, etc.).

Figure 4:
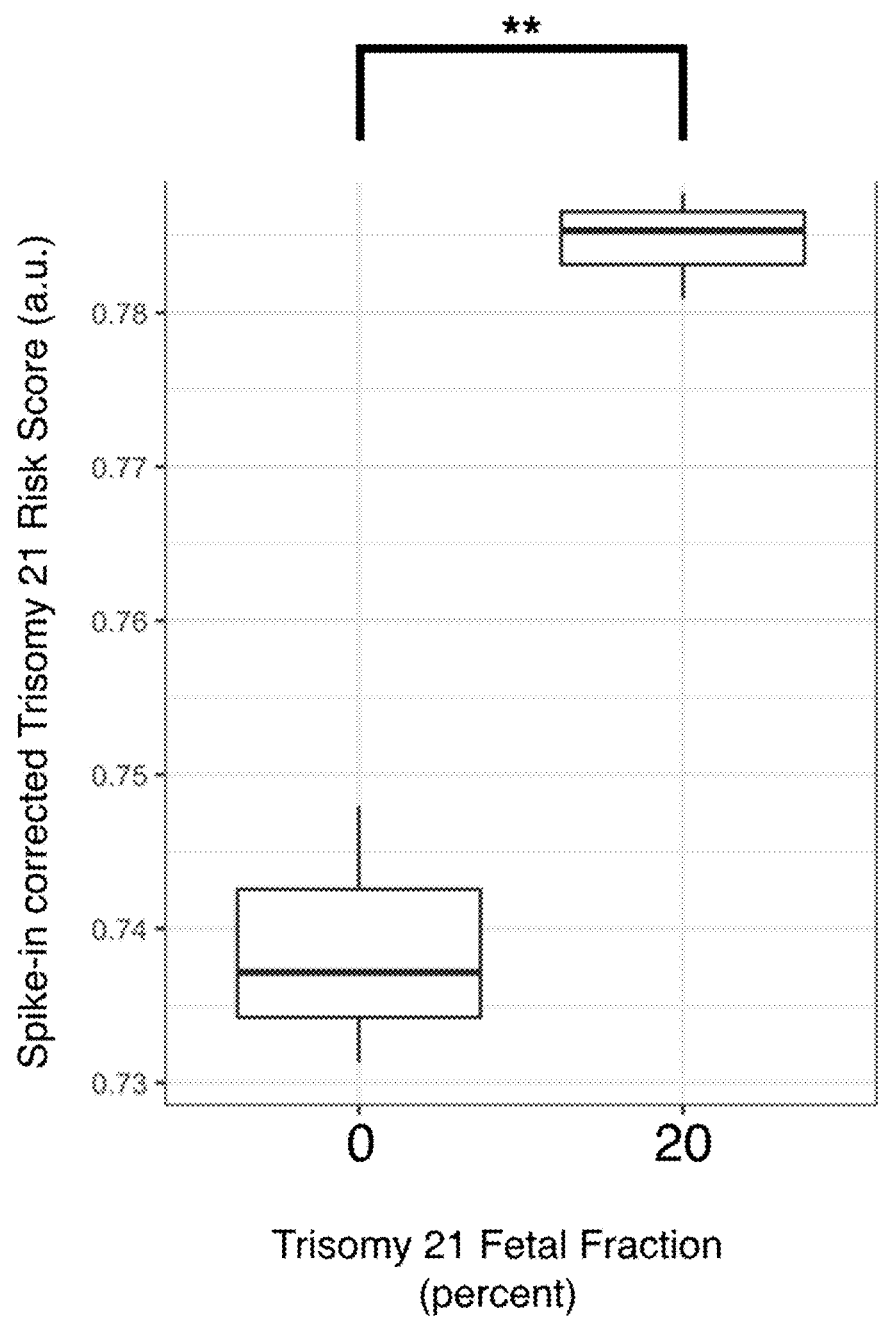
FIG. 4 includes a specific example of results from using spike-in molecules for facilitating diagnosis of trisomy 21.

In examples, as shown in FIGS. 2-3, a medical condition can include one or more genetic disorders including one or more chromosomal abnormalities, where the target sequence region (e.g., of a biological target, such as chromosome 21, etc.) is associated with a first chromosome associated with the chromosomal abnormality, and where facilitating characterization of the medical condition (e.g., prenatal diagnosis of the genetic disorder, etc.) includes facilitating the prenatal diagnosis of the chromosomal abnormality (e.g., based on a comparison between a target-associated count ratio and a reference-associated count ratio; based on any suitable abundance metrics; etc.). In an example, the one or more chromosomal abnormalities can include at least one of a copy number variation condition and a trisomy condition, and where facilitating the prenatal diagnosis of the genetic disorder can include facilitating the prenatal diagnosis of the copy number variation condition and the trisomy condition (e.g., based on the comparison between the target-associated count ratio and the reference-associated count ratio; based on any suitable abundance metrics; etc.). In an example, the one or more chromosomal abnormalities can include a trisomy 21 condition, where the target sequence region is associated with the first chromosome (e.g., chromosome 21, etc.) where the reference sequence region (e.g., of a biological reference, etc.) is associated with a second chromosome (e.g., chromosome 18; any suitable chromosomes; etc.), and/or where facilitating the prenatal diagnosis of the chromosomal abnormality can include facilitating the prenatal diagnosis of the trisomy 21 condition (and/or trisomy 18 condition; etc.) (e.g., based on the comparison between the target-associated count ratio and the reference-associated count ratio; based on any suitable abundance metrics; etc.). In an example (e.g., including a plurality of sets of target-associated molecules and sets of reference-associated molecules; etc.), the medical condition can include one or more chromosomal abnormalities; where the first target sequence region (e.g., with sequence similarity to first target-associated regions of a first set of target-associated molecules; etc.) corresponds to a first loci of a first chromosome; where the second target sequence region (e.g., with sequence similarity to second target-associated regions of a second set of target-associated molecules; etc.) corresponds to a second loci of the first chromosome; where the first reference sequence region (e.g., with sequence similarity to first reference-associated regions of a first set of reference-associated molecules; etc.) corresponds to a first loci of a second chromosome; where generating a second of reference-associated molecules can include generating a second set of reference-associated molecules including second reference-associated regions with sequence similarity to a second reference sequence region corresponding to a second loci of the second chromosome; where determining abundance metrics can include determining a second reference-associated count ratio associated with the second set of reference-associated molecules and the second reference sequence region (e.g., a reference-associated count ratio of a sequence read count for reference molecules including the second reference sequence region, to a sequence read count for the second set of reference-associated molecules; etc.); and/or where facilitating characterization of the medical condition can include facilitating characterization of the chromosomal abnormality based on the first target-associated count ratio (e.g., associated with the first set of target-associated molecules and the first target sequence region; etc.), the second target-associated count ratio (e.g., associated with the second set of target-associated molecules and the second target sequence region; etc.), the first reference-associated count ratio (e.g., associated with the first set of reference-associated molecules and the first reference sequence region; etc.), and the second reference-associated count ratio (and/or any suitable abundance metrics; etc.). In an example, the first chromosome includes chromosome 21; the second chromosome includes chromosome 18; and where facilitating characterization of the medical condition includes facilitating characterization of a trisomy 21 condition and a trisomy 18 condition based on the first target-associated count ratio, the second target-associated count ratio, the first reference-associated count ratio, and the second reference-associated count ratio (and/or any suitable abundance metrics; etc.). In a specific example (e.g., illustrating non-invasive prenatal testing of trisomy 21 using DNA sequencing of spike-in molecules; etc.), as shown in FIG. 8, twenty-six types of target-associated molecules and/or reference-associated molecules (e.g., twenty-six spike-in sequences; etc.) can be designed to co-amplify with associated targets (e.g., associated target sequence regions) located on either chromosome 21 or chromosome 18 in a multiplex PCR; where 0% or 20% Trisomy 21 (T21) affected DNA is added to 33 ng of normal human DNA and synthetic spike-in plasmid (e.g., as shown in FIG. 4); where the human DNA and synthetic spike-in DNA are co-amplified using common primer pairs in a multiplex PCR reaction and prepared for DNA sequencing (e.g., on any suitable sequencing technologies; on the Illumina Miseq; etc.); where spike-in corrected read counts can enable NIPT for T21; where, to compensate for the variance associated with technical replicates in PCR, a spike-in corrected T21 risk score can be calculated using $(R_{21}^{hg}/R_{21}^{spk})/(R_{18}^{hg}/R_{18}^{spk})$; where $R^{spk}$ is the number of reads originating from spike-in sequences (e.g., in relation to chromosome 21 or chromosome 18), and $R^{hg}$ is the number of reads originating from human DNA (e.g., in relation to chromosome 21 or chromosome 18); and where, by applying the correction factor, a significant difference between T21 affected and unaffected samples can be observed (e.g., p=0.0025).

Figure 5:
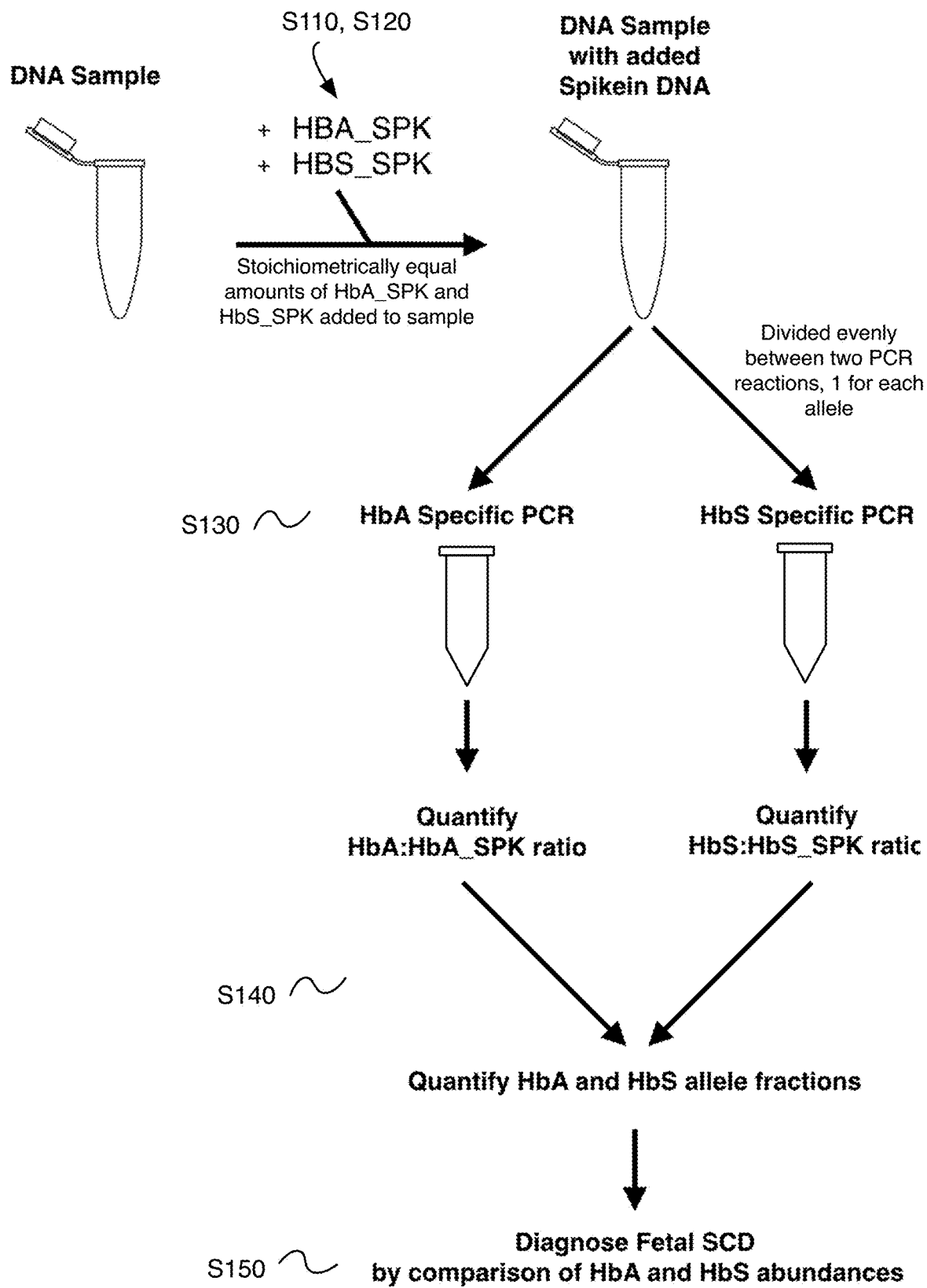
FIG. 5 includes a schematic representation of facilitating diagnosis of sickle cell disease in a variation of an embodiment of a method.

In an example, a medical condition can include one or more genetic disorders including one or more single gene disorders, where the target sequence region (e.g., of a biological target, such as a gene corresponding to the single gene disorder, etc.) includes a mutation associated with the single gene disorder, where the reference sequence region (e.g., of a biological reference, such as the gene corresponding to the single gene disorder; etc.) lacks the mutation, and where facilitating characterization of the medical condition (e.g., facilitating the prenatal diagnosis of the genetic disorder; etc.) includes facilitating the prenatal diagnosis of the single gene disorder (e.g., based on the comparison between the target-associated count ratio and the reference-associated count ratio; based on any suitable abundance metrics; etc.). In an example, a medical condition can include one or more single gene disorders including at least one of a cancer condition and sickle cell disease, where the target sequence region can include a mutation associated with the at least one of the cancer condition and the sickle cell disease, where a reference sequence region lacks the mutation, and/or where facilitating the characterization of the medical condition can include facilitating the characterization of the at least one of the cancer condition and the sickle cell disease (e.g., based on the target-associated count ratio and the reference-associated count ratio; based on any suitable abundance metrics; etc.). In a specific example, as shown in FIG. 5, the method 100 can include sample processing operations and computational processes tailored to facilitating characterization of sickle cell disease (e.g., where HbS mutation is expected to be present for 40-60% of the allele fraction, such as in the context of NIPT; etc.); such as where stoichiometrically equal amounts of target-associated molecules (e.g., "HbS_SPK") and reference-associated molecules (e.g., "HbA_SPK") can be added to a biological sample; where the resulting mixture can be divided evenly between two or more PCR reactions (e.g., a first PCR reaction for co-amplification of target-associated molecules and nucleic acids including the target sequence region; a second PCR reaction for co-amplification of reference-associated molecules and nucleic acids including the reference sequence region; etc.); where first abundance metrics including a target-associated count ratio (e.g., HbS:HbS_SPK ratio) and a reference-associated count ratio (e.g., HbA:HbA_SPK ratio) can be calculated, such as based on sequence reads from sequencing the product of the allele-specific PCR reactions; where second abundance metrics including allele fractions (e.g., for HbA and HbS) can be calculated based on the first abundance metrics; and where a characterization (e.g., diagnoses of fetal sickle cell disease (SCD) can be facilitated (e.g., determined) based on the first abundance metrics and/or second abundance metrics (e.g., based on a comparison of HbA and HbS abundances; etc.).

In an example, a medical condition can include at least one of a chromosomal abnormality and a single gene disorder, where the target sequence region is associated with at least one of a first chromosome (e.g., associated with the chromosomal abnormality, etc.) and a mutation (e.g., associated with the single gene disorder, etc.), where the reference sequence region is associated with at least one of a second chromosome and a lack of the mutation, and where facilitating characterization of the medical condition includes facilitating characterization of the at least one of the chromosomal abnormality and the single gene disorder (e.g., based on one or more abundance metrics; etc.). However, facilitating characterization of chromosomal abnormalities and/or single gene disorders can be performed in any suitable manner.

Figure 6:
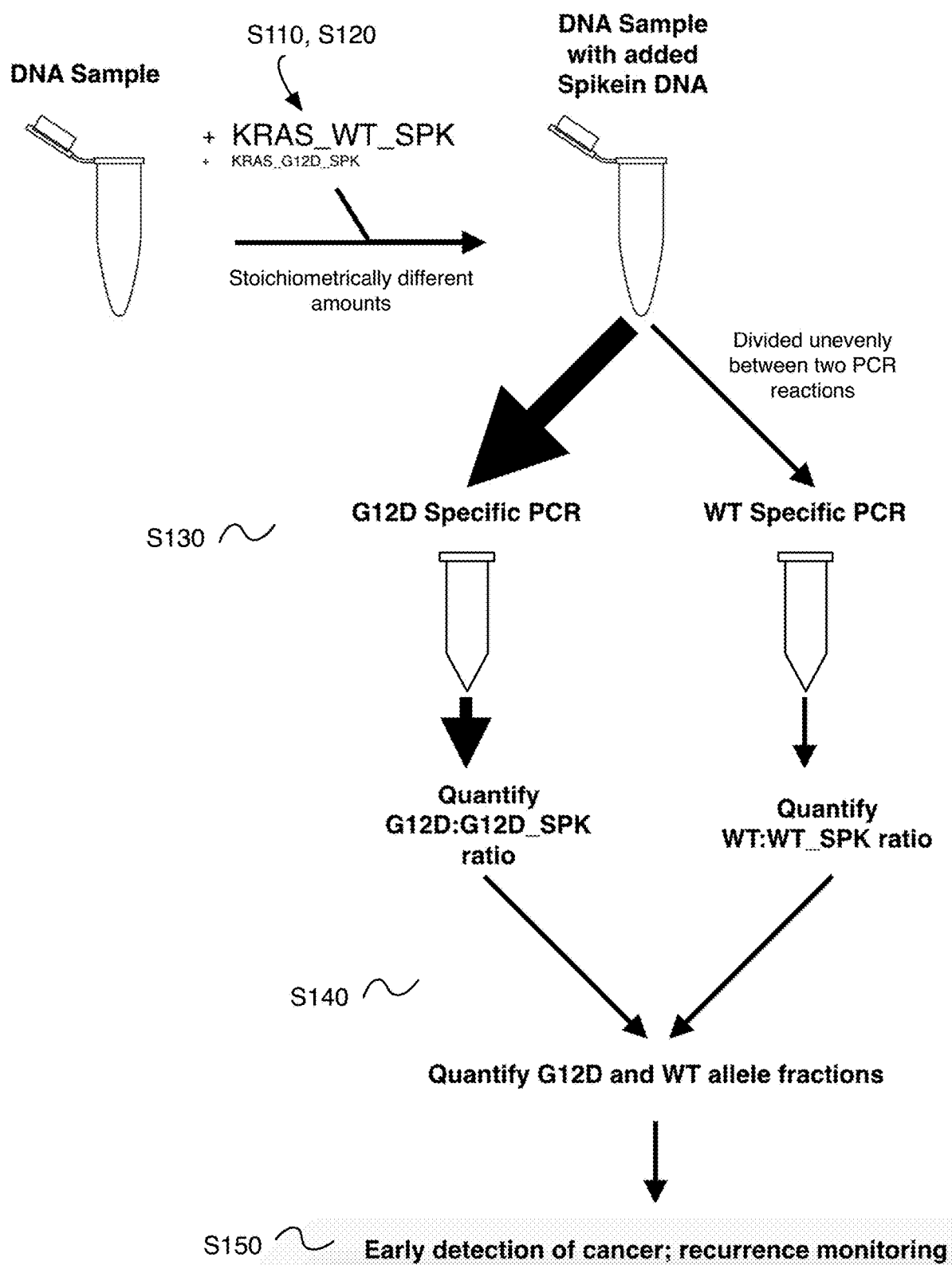
FIG. 6 includes a schematic representation of facilitating diagnosis of rare variant-associated condition in a variation of an embodiment of a method.

In an example, as shown in FIG. 6, the medical condition can include a rare variant-associated condition, such as where a determined abundance ratio can be used in facilitating downstream processes. In an example, the abundance ratio corresponds to an abundance of the set of reference-associated molecules (e.g., associated with wildtype; etc.) that is greater than an abundance of the set of target-associated molecules (e.g., associated with the rare variant; etc.), such as to account for the relative frequency between the rare variant and wildtype (e.g., adding a greater abundance of reference-associated molecules to account for the greater expected frequency of wildtype molecules; etc.), where generation of the at least one spike-in mixture can include: allocation of a first abundance of the biological sample for co-amplification of the set of target-associated molecules and the first nucleic acid molecules (e.g., including the target sequence region associated with the rare variant-associated condition; etc.); and allocation of a second abundance of the biological sample for co-amplification of the set of reference-associated molecules and the second nucleic acid molecules (e.g., including a reference sequence region associated with wildtype; etc.), where the first abundance of the biological sample is greater than the second abundance of the biological sample (e.g., to account for the low expected frequency of the rare variant, for facilitating sufficient amplification; etc.); and/or where facilitating characterization of the medical condition includes facilitating characterization of the rare variant-associated condition (e.g., based on one or more abundance metric; etc.). In a specific example, as shown in FIG. 6, the G12D mutation is expected to be present at very low frequency (e.g., <10% allele fraction), where portions of embodiments of the method 100 can be applied to optimize for sensitive detection of G12D DNA (and/or other suitable rare variant-associated conditions and/or other suitable conditions; etc.), such as including any one or more of: adding reference-associated molecules and target-associated molecules at determined abundance ratios (e.g., adding KRAS_WT_SPK:KRAS_G12D_SPK at a 10:1 stoichiometry, indicated by the smaller lettering for KRAS_G12D_SPK, as shown in FIG. 6; at abundance ratios accounting for the relative frequency of the rare variant to wildtype; etc.); using a greater amount of the sample for the rare variant-specific PCR (e.g., G12D-specific PCR, etc.) than the wildtype-specific PCR (e.g., KRAS_WT specific PCR, etc.); and/or loading a greater amount of the rare variant-associated product (e.g., product of the G12D Specific PCR; etc.) into the sequencer compared to wildtype-specific PCR product (e.g., product from KRAS_WT specific PCR; etc.); where the measurement from the G12D PCR is the <endogenous G12D>:<G12D_SPK> ratio, and the measurement from the WT PCR is the <endogenous WT KRAS>:<WT_SPK> ratio; and given the added 10:1::WT_SPK:G12D_SPK, if measuring <endogenous G12D>/<G12D_SPK>=1, and <endogenous WT KRAS>/<WT_SPK>=1, then a resulting calculation can determine that 1*1/(1*1+1*10)=9.1% of the circulating DNA is KRAS_G12D. In another example (e.g., example B), if measuring <endogenous G12D>:<G12D_SPK>=0.1, and <endogenous WT KRAS>:<WT_SPK>=1, then a resulting calculating can determine the KRAS_G12D allele frequency (AF) to be 0.1*1/(0.1*1+1*10)=0.99%. In examples, applying such approaches (e.g., for facilitating characterization of rare variant-associated conditions; etc.) can overcome limitations of sequencing instruments. In a specific example, if the sequencing error is 1%, then difficulty arises in distinguishing whether measuring a 1% allele fraction is due to the presence of a true variant or due to sequencing error, such as where the limit of detection of the sequencer would then be 1% allele fraction. Target-associated molecules and/or reference-associated molecules (e.g., spike-ins, etc.) can act as an internal control to measure the allele frequency, such as in example B, the lowest allele fraction sequenced is <endogenous G12D>:<G12D_SPK>=10%, which is above the sequencing limit of detection of 1%; however, in examples, portions of embodiments of the method 100 can be applied to calculate G12D to WT allele fraction as 0.99%, which is at the limit of detection of the sequencer, where introducing unbalanced stoichiometry of WT_SPK and G12D_SPK can improve the G12D signal above the noise floor of the DNA sequencer. However, facilitating characterizations of rare variant associated conditions can be performed in any suitable manner.

In variations, facilitating one or more characterizations can be based on one or more fetal fraction measurements (and/or any other suitable data, such as one or more abundance metrics; etc.). For example, facilitating prenatal diagnosis can include facilitating the prenatal diagnosis of one or more genetic disorders based on one or more fetal fraction measurements and/or one or more abundance metrics (e.g., one or more target-associated count ratios, one or more reference-associated count ratios; etc.). However, facilitating characterizations based on fetal fraction measurements can be performed in any suitable manner.

Facilitating characterization of one or more conditions and/or any other suitable portions of embodiments of the method 100 (e.g., determining abundance metrics; etc.) can include applying one or more artificial intelligence approaches (e.g., machine learning approaches, etc.) including any one or more of: supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naive Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a dimensionality reduction method (e.g., principal component analysis, partial lest squares regression, Sammon mapping, multidimensional scaling, projection pursuit, etc.), an ensemble method (e.g., boosting, bootstrapped aggregation, AdaBoost, stacked generalization, gradient boosting machine method, random forest method, etc.), and/or any suitable artificial intelligence approach.

However, facilitating characterization of the one or more conditions S150 can be performed in any suitable manner.

2.6 Facilitating Treatment.

Embodiments of the method 100 can additionally or alternatively include facilitating treatment S160 (e.g., based on one or more abundance metrics; based on one or more characterizations of one or more conditions; etc.), which can function to leverage abundance data to determine, provide, administer, promote, recommend, and/or otherwise facilitate treatment provision (e.g. personalized treatment provision, etc.) for one or more conditions. Facilitating treatment can include applying any suitable techniques associated with analyzing abundance metrics (e.g., for facilitating one or more characterizations; using similar or different statistical operations or algorithms; using the same or different abundance metrics, supplementary data, other suitable data; etc.). Treatments can include any one or more of: therapeutic compositions (e.g., pregnancy-related compositions, medication-based treatments, probiotic-based treatments, topical-based treatments, etc.), surgical treatments, medical device-based treatments, health-related notifications (e.g., transmitted to the subject, to a care provider, etc.) including condition-related and/or treatment-related information derived based on the abundance data; diet-related treatments; cognitive/behavioral treatments; physical therapies; clinical-related treatments (e.g., telemedicine, scheduling a care provider appointment, etc.); alternative medicine-based treatments; environmental-based treatments; and/or any other suitable type of treatments. However, facilitating treatment S160 can be performed in any suitable manner.

However, embodiments of the method 100 can be performed in any suitable manner.

Embodiments of the method 100 and/or system 200 can include every combination and permutation of the various system components and the various method processes, including any variants (e.g., embodiments, variations, examples, specific examples, figures, etc.), where portions of embodiments of the method 100 and/or processes described herein can be performed asynchronously (e.g., sequentially), concurrently (e.g., in parallel), or in any other suitable order by and/or using one or more instances, elements, components of, and/or other aspects of the system 200 and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method 100 and/or system 200 can be embodied and/or implemented at least in part as a machine configured to receive a computer-readable medium storing computer-readable instructions. The instructions can be executed by computer-executable components that can be integrated with embodiments of the system 200. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method 100, system 200, and/or variants without departing from the scope defined in the claims.

We claim:

1. A method for determining the characterization of a prenatal diagnosis of a genetic disorder from a maternal sample associated with a pregnant woman, the method comprising:

generating a set of target-associated molecules comprising:
  target-associated regions with sequence similarity to a target sequence region of a biological target associated with the genetic disorder; and
  target variation regions with sequence dissimilarity to a sequence region of the biological target;

generating a set of reference-associated molecules comprising:
  reference-associated regions with sequence similarity to a reference sequence region of a biological reference; and
  reference variation regions with sequence dissimilarity to a sequence region of the biological reference;

generating a first co-amplified spike-in mixture based on co-amplifying the set of target-associated molecules and first nucleic acid molecules from the maternal sample, wherein the first nucleic acid molecules comprise the target sequence region;

generating a second co-amplified spike-in mixture based on co-amplifying the set of reference-associated molecules and second nucleic acid molecules from the maternal sample, wherein the second nucleic acid molecules comprise the reference sequence region;

sequencing the first and the second co-amplified spike-in mixtures to determine a read count for the biological target, a read count for the set of target-associated molecules, a read count for the biological reference, and a read count for the set of reference associated molecules;

determining a target-associated count ratio based on the read count for the biological target and the read count for the set of target-associated molecules;

determining a reference-associated count ratio based on the read count for the biological reference and the read count for the set of reference-associated molecules; and determining the characterization of the prenatal diagnosis of the genetic disorder based on a comparison between the target-associated count ratio and the reference-associated count ratio.

2. The method of claim 1,
wherein the genetic disorder comprises a chromosomal abnormality,
wherein the target sequence region is associated with a first chromosome associated with the chromosomal abnormality, and
wherein determining the characterization of the prenatal diagnosis of the genetic disorder comprises facilitating the prenatal diagnosis of the chromosomal abnormality based on the comparison between the target-associated count ratio and the reference-associated count ratio.

3. The method of claim 2, wherein the chromosomal abnormality comprises a trisomy condition, wherein the target sequence region is associated with the first chromosome associated with the trisomy condition, and wherein determining the characterization of the prenatal diagnosis of the genetic disorder comprises determining the characterization of the prenatal diagnosis of the trisomy condition based on the comparison between the target-associated count ratio and the reference-associated count ratio.

4. The method of claim 3,
wherein the chromosomal abnormality comprises a trisomy 21 condition,
wherein the target sequence region is associated with the first chromosome comprising chromosome 21,
wherein the reference sequence region is associated with a second chromosome, and
wherein determining the characterization of the prenatal diagnosis of the chromosomal abnormality comprises determining the characterization of the prenatal diagnosis of the trisomy 21 condition based on the comparison between the target-associated count ratio and the reference-associated count ratio.

5. The method of claim 2, wherein the chromosomal abnormality comprises a copy number variation condition, wherein the target sequence region is associated with the copy number variation condition, wherein the reference sequence region is not expected to include the copy number variation, and wherein determining the characterization of the prenatal diagnosis of the genetic disorder comprises determining the characterization of the prenatal diagnosis of the copy number variation condition based on the comparison between the target associated count ratio and the reference-associated count ratio.

6. The method of claim 1,
wherein the genetic disorder comprises a single gene disorder,
wherein the target sequence region comprises a mutation associated with the single gene disorder,
wherein the reference sequence region lacks the mutation, and
wherein determining the characterization of the prenatal diagnosis of the genetic disorder comprises determining the characterization of the prenatal diagnosis of the single gene disorder based on the comparison between the target-associated count ratio and the reference-associated count ratio.

7. The method of claim 1, wherein determining the characterization of the prenatal diagnosis comprises facilitating the prenatal diagnosis of the genetic disorder based on a fetal fraction measurement, the target-associated count ratio, and the reference-associated count ratio.

8. A method for determining the characterization of a medical condition from a biological sample, the method comprising:

generating a first set of target-associated molecules comprising:
first target-associated regions with sequence similarity to a first target sequence region of a biological target associated with the medical condition; and
target variation regions with sequence dissimilarity to a sequence region of the biological target;

generating a first set of reference-associated molecules comprising:
first reference-associated regions with sequence similarity to a first reference sequence region of a biological reference; and
reference variation regions with sequence dissimilarity to a sequence region of the biological reference;

generating at least one spike-in mixture, wherein the generation of the at least one spike-in mixture comprises:
co-amplification of the first set of target-associated molecules and first nucleic acid molecules from the biological sample, wherein the first nucleic acid molecules are associated with the first target sequence region; and
co-amplification of the first set of reference-associated molecules and second nucleic acid molecules from the biological sample, wherein the second nucleic acid molecules are associated with the first reference sequence region;

determining a count for the biological target, a count for the first set of target associated molecules, a count for the biological reference, and a count for the first set of reference-associated molecules, based on sequencing of the at least one spike-in mixture;

determining a first target-associated count ratio and a first reference-associated count ratio based on the count for the biological target, the count for the first set of target associated molecules, the count for the biological reference, and the count for the first set of reference-associated molecules; and determining the characterization of the medical condition based on the first target associated count ratio and the first reference-associated count ratio.

9. The method of claim 8, further comprising:
generating a second set of target-associated molecules comprising second target associated regions with sequence similarity to a second target sequence region; and
determining a second target-associated count ratio associated with the second set of target-associated molecules and the second target sequence region,
wherein determining the characterization of the medical condition comprises determining the characterization of the medical condition based on the first target-associated count ratio, the second target-associated count ratio, and the first reference-associated count ratio.

10. The method of claim 9, wherein the medical condition comprises a chromosomal abnormality, wherein the first target sequence region corresponds to a first loci of a first chromosome, wherein the second target sequence region corresponds to a second loci of the first chromosome, wherein the first reference sequence region corresponds to a first loci of a second chromosome, and wherein the method further comprises:
generating a second set of reference-associated molecules comprising second reference-associated regions with sequence similarity to a second reference sequence region corresponding to a second loci of the second chromosome; and
determining a second reference-associated count ratio associated with the second set of reference-associated molecules and the second reference sequence region,
wherein determining the characterization of the medical condition comprises determining the characterization of the chromosomal abnormality based on the first target-associated count ratio, the second target-associated count ratio, the first reference-associated count ratio, and the second reference-associated count ratio.

11. The method of claim 10, wherein the first chromosome comprises chromosome 21, wherein the second chromosome comprises chromosome 18, and wherein determining the characterization of the medical condition comprises determining the characterization of a trisomy 21 condition and a trisomy 18 condition based on the first target-associated count ratio, the second target-associated count ratio, the first reference-associated count ratio, and the second reference-associated count ratio.

12. The method of claim 9, further comprising: determining an overall target-associated count ratio based on combination of the first target-associated count ratio and the second target-associated count ratio, wherein determining the characterization of the medical condition comprises determining the characterization of the medical condition based on the overall target-associated count ratio and the first reference-associated count ratio.

13. The method of claim 8, wherein generating the first set of target-associated molecules comprises generating the first set of target-associated molecules at a first abundance at least substantially similar to a second abundance of the generated first set of reference-associated molecules.

14. The method of claim 13, further comprising:
generating at least one plasmid comprising the first target-associated regions, the target variation regions, the first reference-associated regions, and the reference variation regions,
wherein generating the first set of target-associated molecules comprises generating the first set of target-associated molecules at the first abundance based on processing of the at least one plasmid, and
wherein generating the first set of reference-associated molecules comprises generating the first set of reference-associated molecules at the second abundance based on the processing of the at least one plasmid.

15. The method of claim 8,
wherein the target variation regions comprise a target variation region comprising at least one of a first substitution, a first insertion, and a first deletion, relative to the sequence region of the biological target, and
wherein the reference variation regions comprise a reference variation region comprising at least one of a second substitution, a second insertion, and a second deletion, relative to the sequence region of the biological reference.

16. The method of claim 8,
wherein the medical condition comprises a genetic disease or disorder comprising at least one of a cancer condition and a single-gene genetic disorder,
wherein the first target sequence region comprises a mutation associated with the at least one of the cancer condition and the single-gene genetic disorder,
wherein the first reference sequence region lacks the mutation, and
wherein determining the characterization of the medical condition comprises determining the characterization of the at least one of the cancer condition and the single-gene genetic disorder, based on the first target-associated count ratio and the first reference-associated count ratio.

17. A method for determining the characterization of a medical condition from a biological sample, the method comprising:
generating a set of target-associated molecules comprising target-associated regions with sequence similarity to a target sequence region of a biological target;
generating of at least one spike-in mixture, wherein the generation of the at least one spike-in mixture comprises amplification of the set of target-associated molecules and first nucleic acid molecules from the biological sample, wherein the first nucleic acid molecules are associated with the target sequence region;
determining at least one abundance metric associated with the biological target and the set of target-associated molecules; and
determining the characterization of the medical condition based on the at least one abundance metric.

18. The method of claim 17, further comprising:
determining an abundance ratio based on the medical condition,
wherein generating the set of target-associated molecules comprises generating the set of target-associated molecules based on the abundance ratio; and
generating a set of reference-associated molecules based on the abundance ratio, wherein the set of reference-associated molecules is associated with a biological reference, and
wherein determining the at least one abundance metric comprises determining the at least one abundance metric associated with the biological target, the set of target associated molecules, the biological reference, and the set of reference-associated molecules, based on the abundance ratio.

19. The method of claim 18,
wherein the medical condition comprises a rare variant-associated condition,
wherein the abundance ratio corresponds to an abundance of the set of reference associated molecules that is greater than an abundance of the set of target-associated molecules,
wherein the generation of the at least one spike-in mixture comprises:
allocation of a first abundance of the biological sample for co-amplification of the set of target-associated molecules and the first nucleic acid molecules; and
allocation of a second abundance of the biological sample for co-amplification of the set of reference-associated molecules and second nucleic acid molecules, wherein the first abundance of the biological sample is greater than the second abundance of the biological sample; and wherein determining the characterization of the medical condition comprises facilitating characterization of the rare variant-associated condition based on the at least one abundance metric.

20. The method of claim 17, wherein the target sequence region is from a set of target sequence regions, wherein the set of target-associated molecules is from sets of target associated molecules associated with different target sequence regions from the set of target sequence regions, wherein the generation of the at least one spike-in mixture comprises:
  pre-amplification with the biological sample based on a set of non-specific primers, to generate a pre-amplified sample; and
  subsampling of the pre-amplified sample to facilitate target sequence region-specific co-amplification based on sets of specific primers associated with the set of target sequence regions and the sets of target-associated molecules.

21. The method of claim 17,
  wherein the medical condition comprises at least one of a chromosomal abnormality and a single gene disorder,
  wherein the target sequence reg10$n$ is associated with at least one of a first chromosome and a mutation,
  wherein determining the characterization of the medical condition comprises facilitating characterization of the at least one of the chromosomal abnormality and the single gene disorder, based on the at least one abundance metric.

22. The method of claim 17, wherein determining the at least one abundance metric comprises determining the at least one abundance metric associated with the biological target and the set of target-associated molecules, based on an output from an abundance measurement technique associated with at least one of a microarray and fluorescence in situ hybridization (FISH) probes.

* * * * *

UNITED STATES PATENT AND TRADEMARK OFFICE
CERTIFICATE OF CORRECTION

PATENT NO. : 11,646,100 B2
APPLICATION NO. : 16/055889
DATED : May 9, 2023
INVENTOR(S) : Tsao et al.

It is certified that error appears in the above-identified patent and that said Letters Patent is hereby corrected as shown below:

In the Claims

In Column 42, in Claim 21, Line 4, delete "reg10n" and insert -- region --, therefor.

Signed and Sealed this
Nineteenth Day of December, 2023

Katherine Kelly Vidal
Director of the United States Patent and Trademark Office